United States Patent [19]
Fujii et al.

[11] Patent Number: 5,914,430
[45] Date of Patent: *Jun. 22, 1999

[54] PROCESS FOR PRODUCING ETHER COMPOUND

[75] Inventors: Yasuyuki Fujii; Hisakazu Furugaki; Katsumi Kita; Mitsuru Uno; Eiko Tamura; Hiromasa Matsumoto, all of Wakayama, Japan

[73] Assignee: Kao Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/675,923

[22] Filed: Jul. 5, 1996

[30] Foreign Application Priority Data

Jul. 12, 1995 [JP] Japan ..................................... 7-176089
Nov. 20, 1995 [JP] Japan ..................................... 7-301150

[51] Int. Cl.$^6$ .................................................... C07C 43/11
[52] U.S. Cl. ........................... 568/618; 568/619; 568/672; 568/697
[58] Field of Search ..................... 568/697, 618, 568/619, 672

[56] References Cited

U.S. PATENT DOCUMENTS 3,954,883   5/1976   Haag .

FOREIGN PATENT DOCUMENTS 41 24 199   1/1993   Germany .
WO 93/02033   2/1993   WIPO .

OTHER PUBLICATIONS

Tetrahedron Letters, vol. 36, No. 24, pp. 4235–4236, 1995, Valerie Bethmont, et al., "An Alternative Catalytic Method to the Williamson's Synthesis of Ethers".
Journal of the Chemical Society, Chemical Communications, pp. 422–423, 1967, Shigeo Nishimura, et al., "Reactions of Cycloalkanones in the Presence of Platinum–Metal Catalysts and Hydrogen".
Journal of the Chemical Society, pp. 5598–5600, 1963, M. Verzele, et al., "A General Synthesis of Ethers".
Purification of Laboratory Chemicals Pervin —pp. 13–14, 40–41, 20–24, 1980.
Fabienne Fache et al, "Reductive 0– and N–alkylations. Alternative Catalytic Methods to Nucleophilic Substitution", Recl. Trav. Chim, Pays–Bas, 115, (1996). pp. 231–238.

Primary Examiner—Gary Geist
Assistant Examiner—Jean F Vollano
Attorney, Agent, or Firm—Oblon, Spivak, McClelland, Maier & Neustadt, P.C.

[57] ABSTRACT

Ether compounds, which are useful as solvents, cosmetics, detergents, lubricants, emulsifiers and so on, are produced by reacting (a) a hydroxy compound with a carbonyl compound of (b) a carbonyl compound under hydrogen atmosphere in the presence of a catalyst with ease and at a low cost. The reaction is carried out while removing out produced water by using a dehydrating agent during the reaction; by distilling off the water by azeotropic dehydration and the like; or by blowing gases such as hydrogen gas to flow through the reaction system.

37 Claims, No Drawings

PROCESS FOR PRODUCING ETHER COMPOUND

BACKGROUN OF THE INVENTION

1. Field of the Invention

The present invention relates to a process for producing ether compounds with ease and at a low cost, which are advantageously useful in a wide variety to applications such as solvents, cosmetics, detergents, lubricants and emulsifiers.

2. Description of the Prior Art

Conventionally, ether compounds such as diethyl ether, dibutyl ether and diethylene glycol diethyl ether have been used as solvents. However, ether compounds having larger molecular weights or those of unsymmetric structures have been scarcely used because of their difficulties to be produced.

In particular, ether compounds are expected to be used as cosmetic oils since they are not so sticky and can be less hydrolyzed than conventionally used ester oils.

Furthermore, the ether compounds have a potential as oils for detergent compositions and new nonionic surfactants and besides as lubricants, emulsifiers and the like.

Although the expectation for the ether compounds has been raised, they cannot easily be produced at low costs at the industrial level.

Known methods for synthesizing ether compounds include, for example, synthesis from alcoholates and alkyl halides (Williamson synthesis); synthesis from alcohols and alkyl sulfates; synthesis from alcohols by dehydration by using acid; and synthesis by addition of alcohols to olefins.

However, in the synthesis from alcoholates and alkyl halides, an alcohol and an equivalent amount of a metal, such as Na and K, or an alkali are necessary to form the corresponding alcoholate. Eventualy a large amount of salts are formed in the reaction. Therefore, this method is not preferred from the industrial point of view.

In the synthesis from alcohols and alkyl sulfates, available alkyl sulfates are restricted to dimethyl sulfate and diethyl sulfate. This method is applicable for synthesizing methyl ether and ethyl ether; it is difficult to synthesize ether compounds having more carbon atoms.

The synthesis by dehydration of alcohols with acid is suitable for synthesizing symmetric ether compounds; it is difficult to synthesize unsymmetric ether compounds by this method.

In the synthesis by addition of alcohols to olefins, the olefin compounds are restricted, and many of them and the catalysts used are very expensive. Further, it is difficult in many cases to recover and reuse the olefins and the catalysts. Accordingly, this method is not industrially suitable.

Besides the methods described above, ether compounds are synthesized from alcohols and carbonyl compounds. For example, J. Chem. Soc., 5598 (1963) and Chem. Commun., 422 (1967) disclose a method in which ether compounds are synthesized by using excess of an alcohol under hydrogen atmosphere at an ordinary pressure in the presence of an acid catalyst.

However, all these methods use a large excess of alcohols and only lower alcohols such as methanol, ethanol and propyl alcohol are applicable, i.e., higher alcohols having more than 6 carbon atoms are not disclosed in the above references.

Further, WO 93/02033 discloses a process for producing polyolethers by reacting at least one polyol with at least one carbonyl compound at a high temperature i.e. 150 to 250° C. in the presence of a hydrogenation catalyst. Additionally, a process for producing a symmetric or unsymmetric ether compound is disclosed in Tetrahedron Letters, Vol. 36, No. 24, pp. 4235–4236 (1995), wherein an aldehyde or a ketone is reacted with a primary or a secondary alcohol in the presence of Pd/C catalyst and then is hydrogenated. In those processes, however, the yields are still low.

As described above, the ether compounds can not widely be used because of difficulty in producing them while they are expected to be applied to various uses. Accordingly, a process in which an ether compound can easily be produced at low costs have been desired.

DESCRIPTION OF THE INVENTION

A purpose of the present invention is to provide a process for producing an ether compound with ease at a low cost at an improved production rate, which is useful for solvents, cosmetics, detergents, lubricants, emulsifiers and the like.

The inventors have made intensive investigations to find a simple and inexpensive process for producing a widely applicable ether compound at a high production rate as an improvement of the above shown hydrogenational decomposition. As a result, they have found that an ether compound can be obtained in one step at a high yield or production rate by carrying out the reaction using as the starting material (a) a hydroxy compound compound with a carbonyl compound, or (b) carbonyl compounds by itself, reacting it under hydrogen gas atmosphere in the presence of a catalyst, while removing water produced by the reaction.

The invention provides a process for producing an ether compound by reacting (a) a hydroxy compound with a carbonyl compound or (b) a carbonyl compound, under hydrogen gas atmosphere in the presence of a catalyst, while removing out water produced by the reaction.

DETAILED DESCRIPTION OF THE INVENTION

The embodiments of the present invention will be explained below in detail.

In the present invention, (a) a hydroxy compound and a carbonyl compound or (b) a carbonyl compound is reacted while removing water produced by the reaction.

Examples of the hydroxy compound used in the present invention include compounds represented by the formula (1):

$$R_1\text{—}(OA)_n\text{—}OH \quad (1)$$

[wherein, $R_1$ represents a straight or branched alkyl or alkenyl group having 1 to 40 carbon atoms, or a cycloalkyl group having 3 to 12 carbon atoms; A represents an alkylene group having 2 to 12 carbon atoms which may have a hydroxyl group;, two or more A's may be the same as or different from one another; n is a number of 0 to 500].

$R_1$ is preferebly a straight or branched alkyl group having 1 to 24 carbon atoms or a cycloalkyl group having 5 to 8 carbon atoms, more preferably a straight alkyl group having 3 to 24, particularly 6 to 22 carbon atoms or a cycloalkyl having 5 to 7 carbon atoms.

A is preferably a straight or branched alkylene group having 2 to 6 carbon atoms which may have a hydroxyl group, including for example, groups of ethylene, propylene, trimethylene, tetramethylene, 1,2-butylene, pentylene, hexylene and 2-hydroxypropylene. Among them, ethylene, propylene, trimethylene and tetramethylene are preferable, more preferably, a straight or branched alkylene group having 2 to 3 carbon atoms, particularly ethylene or propylene group are used.

The n is preferably a number of 0 to 200, more preferably, 0 to 30. Two or more A's may be the same as or different from one another, and the oxyalkylene groups, OA, of the formula (1) may be bonded to one another either in the form of block or at random.

Furthermore, as another hydroxy compound, polyhydric compounds having 2 or more hydroxyl groups can be used in the present invention. Examples thereof include polyhydric alcohols and derivatives thereof having 2 to 10 hydroxyl groups. More specifically, examples thereof include a diol having 2 to 20 carbon atoms, glycerol, trimethylol ethane, trimethylol propane, pentaerythrytol, sacharide and alkylene oxide adducts thereto (addition molar numbers of 0 to 500). Among them, a diol having 2 to 20 carbon atoms, preferably 2 to 10 carbon atoms, glycerin and ethylene oxide adducts thereto (addition molar numbers of 0 to 200) are particularly preferred.

These hydroxy compounds can be used alone or in a mixture of two or more of them.

Examples of the carbonyl compound used in the present invention include compounds represented by the formula (2):

(2)

[wherein, $R_2$ and $R_3$ represent a hydrogen atom or a straight or branched alkyl or alkenyl group having 1 to 20 carbon atoms. $R_2$ and $R_3$ may be the same as or different from one another. $R_2$ and $R_3$ may be combined with each other to form a cyclic structure].

Among these carbonyl compounds, a linear ketone having 1 to 12 carbon atoms, an aldehyde having 1 to 12 carbon atoms or a cyclic ketone having 5 to 8 carbon atoms is preferred. Among them, linear ketones having 3 to 6 carbon atoms including acetone, methylethyl ketone, methylisobutyl ketone (4-methyl-2-pentanone); aliphatic aldehyde having 1 to 12, preferably 3 to 8 carbon atoms, such as formaldehyde, paraformaldehyde, acetoaldehyde, butylaldehyde, octylaldehyde and dodecylaldehyde; and cyclic Hetones having 5 to 7 carbon atoms inculding cyclohexane are particluraly preferred. Most preferrd are acetone, methylethyl ketone, methylisobutyl ketone (4-methyl-2-pentanone).

In addition, as other carbonyl compounds, polyvalent carbonyl compounds having 2 or more carbonyl groups are included. Preferred are compounds having 2 to 10 carbonyl groups, for examples, linear or cyclic dicarbonyl compounds having 2 to 20 carbon atoms. Linear dicarbonyl compounds having 2 to 10 carbon atoms and cyclohexanedione are particularly preferred.

These carbonyl compounds may be used alone or as a mixture of two or more species.

A typical reaction for producing an ether compound by reacting a hydroxy compound represented by the formula (1) with a carbonyl compound represented by the formula (2) in the present invention under hydrogen atmosphere using a catalyst is shown by the following reaction formula 1.

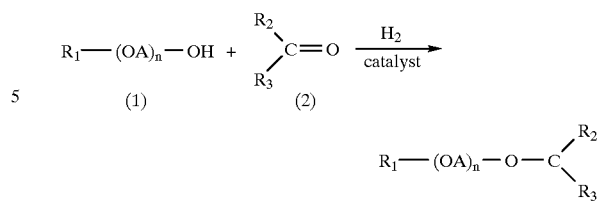

And a typical reaction for producing an ether compound by reacting a carbonyl compound represented by the formula (2) in the present invention under hydrogen atmosphere using a catalyst is shown in the following reaction formula 2.

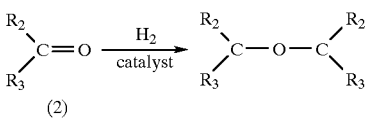

(2)

Though the charging ratio of the hydroxy compound represented by the formula (1) to the carbonyl compound represented by the formula (2) in the present process is not specifically limited, a preferred molar ratio of hydroxy compound/carbonyl compound is usually 50/1 to 1/50, particularly, 20/1 to 1/20, more particularly, 10/1 to 1/10. If the hydroxy compound has a low molecular weight and can easily be removed, the hydroxy compound is preferably used in an excess amount to react the whole amount of the carbonyl compound. If the hydroxy compound has a large molecular weight and the carbonyl compound has a low molecular weight and can be easily removed, the carbonyl compound is preferably used in an excess amount to react the whole amount of the hydroxy compound which is difficult to remove. A mole ratio of the hydroxy compound/carbonyl compound falling outside the range described above does not exert so much influence on the yield but is not economical.

In the present invention, the catalysts used in reacting (a) the hydroxy compound and the carbonyl compound, or (b) the carbonyl compounds include palladium or palladium compounds such as palladium hydroxide and palladium oxide, ruthenium, rhodium or platinum, ruthenium oxide, rhodium oxide, and platinum oxide. Further, iridium, osmium and rhenium can be used as well. These catalysts may be supported on a carrier such as carbon, silica-alumina, zeolite, alumina or silica. Among these catalysts, preferred are palladium catalysts, and more preferred is palladium, palladium hydroxide; or palladium oxide, supported on carbon, silica-alumina, alumina or silica. Palladium supported on carbon is particularly preferred.

The supported amount when the catalyst is supported on each carrier is in the range of 2 to 10% by weight based on the weight of a carrier. The supported catalysts may include 20 to 60% by weight of water.

When the catalyst is supported in an amount of 5% by weight based on the weight of the carrier, the supported catalyst is used preferably in an amount of 0.1 to 20% weight based on the weight of the carbonyl compound used. Even when it is less than 0.1% by weight, the reaction can be conducted, however, it is not preferred since the reaction proceeds slow. Meanwhile, when it exceeds 20% by weight, the reaction proceeds fast, but it is not preferred since side reactions also appear. The amount is more preferably 0.5 to 15 weight %.

The catalyst can be used in any pH range but the catalyst having a pH of 8 or lower is preferred, more preferably in the range from 2 to 8, the most preferably in the range from 3 to 7.5. In this case, the pH of the catalyst means a pH of an aqueous solution obtained by dispersing 2 g of the catalyst powder in 30 g of ion-exchanged water.

In the present invention, (a) the hydroxy compound and the carbonyl compound, or (b) the carbonyl compounds are reacted in hydrogen gas atmosphere. The hydrogen gas pressure is not specifically limited and may be either at the atomspheric pressure or an increased pressure. It is preferably from the atmospheric pressure to 300 kg/cm$^2$, further preferably from the atmospheric pressure to 200 kg/cm$^2$, particularly preferably from the atmospheric pressure to 150 kg/cm$^2$.

In the present invention, the reaction temperature in reacting (a) the hydroxy compound with the carbonyl compound or (b) the carbonyl compounds are not specifically limited and are preferably 10 to 200° C., particularly preferably 50 to 180° C.

In each of (a) and (b) described above, the reaction time can suitably be selected depending on the reaction temperature, the hydrogen gas pressure and the catalyst's amount, and is usually 1 to 24 hours, preferably 1 to 12 hours in each case.

In the reaction described above, the reaction can be carried out without using a solvent but can be carried out in a diluted form with a suitable solvent. Any solvents can be used as long as they are inert to the hydrogenation reaction, for example, solvents such as n-pentane, n-hexane, n-heptane, n-octane, n-decane, and petroleum ether, and ether solvents such as dibutylether, dihexylether and tetrahydrofuran.

The reaction in the present invention is carried out while removing produced water by at least one method selected from the group consisting of:

(1) being in the presence of a dehydrating agent;
(2) distillating off the water; and
(3) blowing hydrogen gas to flow through the reaction system.

That is, the reaction in the present invention is carried out while removing the produced water, which means not only removing out the water from the reaction system but also removing the water in the reaction system with use of dehydrating agents by way of adsorption or a reaction. Concrete methods for removing the water include; carrying out the reaction in the presence of a dehydrating agent; distilling the water off by azeotropic dehydration and the like; and blowing gases such as hydrogen gas through the reaction system.

Further methods for removing the water are included; distillating off the water by an azeotropic dehydration while returning back into the reaction system unreacted raw materials or ether compounds as reaction products having come out of the reaction system together with the water; removing the water while blowing hydrogen gas and conducting an azeotropic dehydrating.

In the method for removing water by carrying out the reaction in the presence of a dehydrating agent in the present invention, the dehydrating agent used includes so-called drying agents used for drying liquids.

In general, the dehydrating ability of the dehydrating agent is attained on the basis of physical or chemical adsorption of water or a chemical reaction. The dehydrating agent used in the present invention is not specifically limited by the mechanism of the dehydrating ability, and any dehydrating agents can be used as long as they have a dehydrating ability or a water-absorbing ability and substantially remove out the produced water, causing the intended etherification to proceed rapidly. It is not preferable to use strong acids and strong alkalis as they are, which cause reactions being substantially different from the dehydration, for example, dissolving the catalysts or causing dimerization to carbonyl compounds. However, it is a matter of course that strong acids and strong alkalis can be used as well if some measures are employed so that they are not involved directly in the reaction system.

The preferred dehydrating agents used in the resent invention include inorganic salts such as magnesium sulfate, sodium sulfate, calcium sulfate, copper sulfate, and calcium chloride, preferably anhydrous ones, hydroxides such as calcium hydroxide, oxides such as magnesium oxide, crystalline zeolite such as molecular sieves, and silica gel. However, the dehydrating agents are not necessarily limited to these compounds. Among these dehydrating agents, the anhydrous inorganic salts, and the crystalline zeolite are preferred. Further, anhydrous magnesium sulfate, anhydrous sodium sulfate, anhydrous calcium sulfate, and molecular sieve are preferred, and anhydrous magnesium sulfate is particularly preferred.

In the present invention, the amount of the dehydrating agent is not specifically limited and is preferably 0.1 to 100 molar %, more preferably 0.1 to 80 molar %, particularly preferably, 0.1 to 50 molar % based on the hydroxy compound or carbonyl compound as the raw material. The method for removing water by carrying out the reaction in the presence of such dehydrating agents is preferred very much since a specific reactor is not needed, and the water can easily be removed only by adding dehydrating agents.

Further, in the present invention, the produced water by the reaction can also be removed out of the reaction system by distilling it off. A method for distilling off the water is not specifically limited and includes, for example, a method by azeotropic dehydration. In this case, it is preferred to distill off the water together with unreacted raw materials or reaction products, circulating the unreacted raw materials into the reaction system by separating the water by a fractional distillation, by a phase separation or by a treatment with a dehydrating agents. This circulating step can be made continuously or stepwise, either during the reaction or not. When the raw materials can not be trapped sufficiently, it is preferable to add further raw materials.

As a method for carrying out the azeotropic dehydration, there are a method in which the reaction and the distillation of the water are carried out continuously by use of an azeotropic dehydration apparatus, and a method in which the reaction and then removing out the water are carried out stepwise, e.g., a method in which after once the reaction is carried out, the azeotropic dehydration is carried out, then the reaction is carried out again. The reaction is preferably carried out continuously in order to cause the reaction to proceed smoothly. Further, in order to carry out efficiently the dehydration, the azeotropic dehydration may be carried out while flowing though hydrogen gas.

In the method for carrying out the reaction while removing out the water by the azeotropic dehydration in the present invention, it is preferable to use solvents as an azeotropic solvent which exert no adverse effects on the reaction. Concrete examples thereof include toluene, xylene and benzene. However, it is not necessarily limited to them. And the amount of the solvent is not specifically limited when the solvent is used in the reaction, 1 to 2 times as much an amount in volume as reaction liquid are preferred.

By such an azeotropic dehydration, there is an advantage that the water can be removed out effectively.

Further, in the present invention, produced water by the reaction can be removed out of the reaction system by carrying out the reaction while blowing gases such as hydrogen gas onto or through the reaction liquid. By blowing hydrogen gas and so on into the reaction liquid is particularly preferable to remove out the water effectively. The flow amount of hydrogen gas used in the present invention can be selected according to the scale of the reaction and is preferably 0.01 to 30 liters/min, more preferably 0.01 to 10 liters/min, for example, in the scale of 0.5 liter. The flow amount of hydrogen gas controlled to 0.01 liter/min or more makes it easy to remove out the water of the reaction system and accelerates the reaction. The flow amount of hydrogen gas controlled to 30 liters/min or less is preferred since a reduced amount of the hydroxy compound or carbonyl compound as the raw materials is removed together with the water. In this case, however, the hydroxy compound or carbonyl compound removed together with the water can be returned again to the reactor after removing the water, for example, by fractional distillation or a dehydrating agent, to thereby continue the reaction without stagnation. The blowing of the hydrogen gas may be continuously or intermittently conducted during the reaction. The continuous blowing is preferred in order to cause the reaction to proceed smoothly.

Further, the hydrogen gas blown into the reaction system may be discharged in the air as it is, but in order to use the hydrogen gas effectively, it is efficient and therefore preferred to return again the hydrogen gas coming out of the system to the system via a circulating line to be used for the reaction while circulating.

Such methods as removing out the water while blowing the hydrogen gas has such advantages that no reagents are further added and that hydrogen gas can easily be separated from water and pro-treatment is simple.

EXAMPLES

The present invention will now be explained below in more detail with reference to examples, but the resent invention shall not be restricted to these examples.

Example A-1

Production of 1,3-dimethyl butyl tetradecyl ether

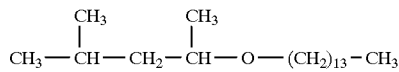

197 g (0.5 mol) of tetradecyl alcohol, 100 g (1.0 mol) of 4-methyl-2-pentanone, 2.1 g of 5% Pd—C (pH 6.6) as a catalyst and 8.6 g (0.07 mol) of anhydrous magnesium sulfate as a dehydrating agent were charged into a 500 ml of autoclave equipped with a hydrogen gas-introducing tube and a stirrer, and the mixture was stirred at 100 kg/cm$^2$ of hydrogen pressure at 150° C. for 5 hours.

After completion of the reaction, the catalyst and magnesium sulfate were removed by filtration, and excess 4-methyl-2-pentanone was removed under reduced pressure. Further, distillation under reduced pressure (143° C./1 Torr) was carried out to obtain 148 g (0.49 mol) of intended 1,3-dimethyl butyl tetradecyl ether as a colorless, transparent liquid.

The isolation yield was 99%.

Comparative Example A-1

The reaction was carried out in the same manner as that in Example A-1, except that anhydrous magnesium sulfate was not added, whereby 109 g (0.37 mol) of 1,3-dimethyl butyl tetradecyl ether was obtained as a colorless, transparent liquid.

The isolation yield was 73%.

Examples A-2 to 7

The hydroxy compounds and the carbonyl compounds shown in Table A-1 were reacted in the presence of the catalysts and the dehydrating agents shown in Table A-1 in the same manner as that in Example A-1, except that the reaction conditions were changed as shown in Table A-1.

The resulting products and the isolation yields thereof are shown in Table A-1.

Comparative Examples A-2 to 7

The hydroxy compounds and the carbonyl compounds shown in Table A-2 were reacted in the presence of the catalysts shown in Table A-2 in the same manner as that in Comparative Example A-1, except that the reaction conditions were changed as shown in Table A-2.

The resulting products and the isolation yields thereof are shown in Table A-2.

TABLE A-1

| | | Hydroxy compound | Carbonyl compound | Catalyst | Dehydrating agent | Reaction condition | Product and Isolation yield |
|---|---|---|---|---|---|---|---|
| Ex. | A-1 | tetradecyl alcohol 107 g (0.5 mol) | 4-methyl-2-pentanone 100 g (1.0 mol) | 5% Pd—C (pH 6.6) 2.1 g | anhydrous magnesium sulfate 8.6 g (0.07 mol) | H$_2$ pressure: 100 kg/cm$^2$ 150° C., 5 h. | 1,3-dimethylbutyl tetradecyl ether 148 g (0.49 mol), 99% |
| | A-2 | hexadecyl alcohol 121 g (0.5 mol) | 4-methyl-2-pentanone 100 g (1.0 mol) | 5% Pd—C (pH 6.6) 2.4 g | anhydrous magnesium sulfate 8.6 g (0.07 mol) | H$_2$ pressure: 100 kg/cm$^2$ 150° C., 5 h. | 1,3-dimethylbutyl hexadecyl ether 161 g (0.49 mol), 99% |
| | A-3 | tetradecyl alcohol 107 g (0.5 mol) | 4-methyl-2-pentanone 100 g (1.0 mol) | 5% Pd—Al$_2$O$_3$ (pH 5.0) 2.1 g | anhydrous magnesium sulfate 8.6 g (0.07 mol) | H$_2$ pressure: 100 kg/cm$^2$ 150° C., 8 h. | 1,3-dimethylbutyl tetradecyl ether 110 g (0.37 mol), 74% |
| | A-4 | octadecyl alcohol 135 g (0.5 mol) | methylethyl ketone 72 g (1.0 mol) | 5% Pd—C (pH 4.0) 2.7 g | anhydrous magnesium sulfate 7.1 g (0.05 mol) | H$_2$ pressure: 100 kg/cm$^2$ 150° C., 8 h. | 1-methylpropyl octadecyl ether 160 g (0.49 mol), 98% |

TABLE A-1-continued

| | | Hydroxy compound | Carbonyl compound | Catalyst | Dehydrating agent | Reaction condition | Product and Isolation yield |
|---|---|---|---|---|---|---|---|
| | A-5 | tetradecyl alcohol 107 g (0.5 mole) | acetone 87 g (1.5 mol) | 5% Pd—C (pH 4.0) 2.1 g | anhydrous magnesium sulfate 13.6 g (0.10 mol) | $H_2$ pressure: 100 kg/cm$^2$ 150° C., 8 h. | isopropyl tetradecyl ether 127 g (0.49 mol), 99% |
| | A-6 | diethylene glycol monobutyl ether 97 g (0.6 mol) | butyl aldehyde 130 g (1.8 mol) | 5% Pd—C (pH 4.0) 1.9 g | anhydrous magnesium sulfate 9.6 g (0.08 mol) | $H_2$ pressure: 100 kg/cm$^2$ 150° C., 8 h. | diethylene glycol dibutyl ether 129 g (0.59 mol), 99% |
| | A-7 | triethylene glycol monododecyl ether 127 g (0.4 mol) | butyl aldehyde 86 g (1.2 mol) | 5% Pd—C (pH 4.0) 2.5 g | anhydrous magnesium sulfate 7.2 g (0.06 mol) | $H_2$ pressure: 100 kg/cm$^2$ 150° C., 8 h. | triethylene glycol butyldodecyl ether 148 g (0.39 mol), 99% |

TABLE A-2

| | | Hydroxy compound | Carbonyl compound | Catalyst | Dehydrating agent | Reaction condition | Product and Isolation yield |
|---|---|---|---|---|---|---|---|
| Comp. Ex. | A-1 | tetradecyl alcohol 107 g (0.5 mol) | 4-methyl-2-pentanone 100 g (1.0 mol) | 5% Pd—C (pH 6.6) 2.1 g | — | $H_2$ pressure: 100 kg/cm$^2$ 150° C., 5 h. | 1,3-dimethylbutyl tetradecyl ether 109 g (0.37 mol), 73% |
| | A-2 | hexadecyl alcohol 121 g (0.5 mol) | 4-methyl-2-pentanone 100 g (1.0 mol) | 5% Pd—C (pH 6.6) 2.4 g | — | $H_2$ pressure: 100 kg/cm$^2$ 150° C., 5 h. | 1,3-dimethylbutyl hexadecyl ether 112 g (0.35 mol), 69% |
| | A-3 | tetradecyl alcohol 107 g (0.5 mol) | 4-methyl-2-pentanone 100 g (1.0 mol) | 5% Pd—Al$_2$O$_3$ (pH 5.0) 2.1 g | — | $H_2$ pressure: 100 kg/cm$^2$ 150° C., 8 h. | 1,3-dimethylbutyl tetradecyl ether 33 g (0.11 mol), 22% |
| | A-4 | octadecyl alcohol 135 g (0.5 mol) | methylethyl ketone 72 g (1.0 mol) | 5% Pd—C (pH 4.0) 2.7 g | — | $H_2$ pressure: 100 kg/cm$^2$ 150° C., 8 h. | 1-methylpropyl octadecyl ether 109 g (0.33 mol), 66% |
| | A-5 | tetradecyl alcohol 107 g (0.5 mole) | acetone 87 g (1.5 mol) | 5% Pd—C (pH 4.0) 2.1 g | — | $H_2$ pressure: 100 kg/cm$^2$ 150° C., 8 h. | isopropyl tetradecyl ether 92 g (0.36 mol), 72% |
| | A-6 | diethylene glycol monobutyl ether 97 g (0.6 mol) | butyl aldehyde 130 g (1.8 mol) | 5% Pd—C (pH 4.0) 1.9 g | — | $H_2$ pressure: 100 kg/cm$^2$ 150° C., 8 h. | diethylene glycol dibutyl ether 92 g (0.42 mol), 70% |
| | A-7 | triethylene glycol monododecyl ether 127 g (0.4 mol) | butyl aldehyde 86 g (1.2 mol) | 5% Pd—C (pH 4.0) 2.5 g | — | $H_2$ pressure: 100 kg/cm$^2$ 150° C., 8 h. | triethylene glycol butyldodecyl ether 102 g (0.27 mol), 68% |

Example A-8

Production of dicyclohexyl ether

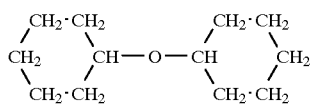

147 g (1.5 mol) of cyclohxanone, 100 g (1.0 mol) of cyclohexanol, 5 g of 5% Pd—C (pH 6.6) as a catalyst and 13 g (0.1 mol) of anhydrous magnesium sulfate as a dehydrating agent were charged into a 500 ml autoclave equipped with a hydrogen gas-introducing tube and a stirrer, and the contents were stirred at 100 kg/cm$^2$ of hydrogen pressure at 180° C. for 7 hours.

After the completion of the reaction, the autoclave was cooled down to room temperatures, and the autoclave was exhausted of hydrogen gas and opened. The catalyst and magnesium sulfate were removed from the reaction solution by filtration, and then analyzing by the gas chromatography was carried out. The result thereof showed that the apparent conversion rate of cyclohexanol was 97% and the yield of dicyclohexyl ether was 95%.

Comparative Example A-8

Dicyclohexyl ether was obtained in the same manner as that in Example A-8, except that anhydrous magnesium sulfate was not added. The result thereof showed that the apparent conversion rate of cyclohexanol was 81% and the yield of dicylohexyl ether was 78%.

Example A-9

Production of 1,3-dimethyl butyl tetradecyl ether

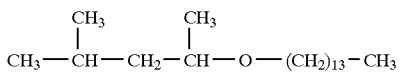

80 g (0.37 mol) of tetradecyl alcohol, 150 g (1.5 mol) of 4-methyl-2-pentanone and 1.6 g of 5% Pd—C (pH 4.0) as a catalyst were charged into a 500 ml of autoclave equipped with a hydrogen gas-introducing tube and a stirrer, and the contents were stirred under 100 kg/cm$^2$ of hydrogen pressure at 150° C. for 8 hours to carry out the reaction of the first step.

After completion of the reaction of the first step, the catalyst was removed by filtration, and a 500 ml flask equipped with a dehydration-refluxing tube and a stirrer was charged with the filtrate. The mixture of 4-methyl-2-pentanone and water, which was distilled by azeotropy, was separated into phases in the dehydration-refluxing tube to remove water. Then, the solution obtained after finishing azeotropic dehydration and the catalyst were returned again into the autoclave to carry out the reaction of the second step at 100 kg/cm² of hydrogen pressure at 150° C. for 7 hours. After completion of the reaction of the second step, the catalyst was removed by filtration, and excess 4-methyl-2-pentanone was removed under reduced pressure. Further, distillation under reduced pressure (143° C./1 Torr) was carried out to obtain 107 g (0.36 mol) of intended 1,3-dimethyl butyl tetradecyl ether as a colorless, transparent liquid.

The isolation yield was 97%.

Comparative Example A-9

80 g (0.37 mol) of tetradecyl alcohol, 150 g (1.5 mol) of 4-methyl-2-pentanone, and 1.6 g of 5% Pd—C (pH 4.0) as a catalyst were charged into a 500 me autoclave equipped with a hydrogen gas-introducing tube and a stirrer, and the reaction was carried out at 100 kg/cm² of hydrogen pressure at 150° C. for 15 hours.

After completion of the reaction, the catalyst was removed by filtration, and excess 4-methyl-2- pentanone was removed under reduced pressure. Further, distillation under reduced pressure (143° C./1 Torr) was carried out to obtain 86 g (0.29 mol) of intended 1,3-dimethyl butyl tetradecyl ether as a colorless and transparent liquid.

The isolation yield was 78%.

Example A-10

Production of 1,3-dimethyl butyl hexadecyl ether

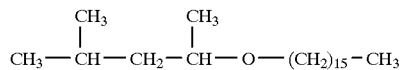

90 g (0.37 mol) of hexadecyl alcohol, 150 g (1.5 mol) of 4-methyl-2-pentanone and 1.8 g of 5% Pd—C (pH 4.0) as a catalyst were charged into a 500 ml autoclave equipped with a hydrogen gas-introducing tube, a stirrer and a dehydration-refluxing device, and the contents were stirred at 20 kg/cm² of hydrogen pressure at 150° C. for 12 hours while carrying out azeotropic dehydration. The mixture of 4-methyl-2-pentanone and water, which was distilled by azeotropy during the reaction, was separated into phases in a fractionating tube installed in the dehydration-refluxing device and only 4-methyl-2-pentanone was refluxed continuously in the autoclave.

After completion of the reaction, the catalyst was removed by filtration, and excess 4-methyl-2-pentanone was removed under reduced pressure. Further, distillation under reduced pressure (145° C./0.3 Torr) was carried out to obtain 115 g (0.35 mol) of intended 1,3-dimethyl butyl hexadecyl ether as a colorless, transparent liquid.

The isolation yield was 95%.

Comparative Example A-10

90 g (0.37 mol) of hexadecyl alcohol, 150 g (1.5 mol) of 4-methyl-2-pentanone and 1.8 g of 5% Pd—C (pH 4.0) as a catalyst were charged into a 500 me autoclave equipped with a hydrogen gas-introducing tube and a stirrer, and the contents were stirred at 20 kg/cm² of hydrogen pressure at 150° C. for 12 hours.

After completion of the reaction, the catalyst was removed by filtration, and excess 4-methyl-2-pentanone was removed under reduced pressure. Further, distillation under reduced pressure (145° C./0.3 Torr) was carried out to obtain 75 g (0.23 mol) of intended 1,3-dimethyl butyl hexadecyl ether as a colorless, transparent liquid.

The isolation yield was 62%.

Examples A-11 to 13

The hydroxy compounds and the carbonyl compounds shown in Table A-3 were reacted in the presence of the catalysts shown in Table A-3 in the same manner as that in Example A-10, except that the reaction conditions were changed as shown in Table A-3.

The resulting products and the isolation yields thereof are shown in Table A-3 together with the results of Examples A-9 and 10.

Comparative Examples A-11 to 13 the hydroxy compounds and the carbonyl compounds shown in Table A-4 were reacted in the presence of the catalysts shown in Table A-4 in the same manner as that in Comparative Example A-10, except that the reaction conditions were changed as shown in Table A-4.

The resulting products and the isolation yields thereof are shown in Table A-4 together with the results of Comparative Examples A-9 and 10.

TABLE A-3

| | | Hydroxy compound | Carbonyl compound | Catalyst | Reaction condition | Product and Isolation yield |
|---|---|---|---|---|---|---|
| Ex. | A-9 | tetradecyl alcohol 80 g (0.37 mol) | 4-methyl-2-pentanone 150 g (1.5 mol) | 5% Pd—C (pH 4.0) 1.6 g | First Stage Reaction: $H_2$ press.: 100 kg/cm² 150° C., 8 h. Azeotropic dehydration after First Stage Reaction Second Stage Reaction: $H_2$ press.: 100 kg/cm² 150° C., 7 h. | 1,3-dimethylbutyl tetradecyl ether 107 g (0.36 mol), 97% |
| | A-10 | hexadecyl alcohol 90 g (0.37 mol) | 4-methyl-2-pentanone 150 g (1.5 mol) | 5% Pd—C (pH 4.0) 1.8 g | While azeotropic dehydration $H_2$ press.: 20 kg/cm² 150° C., 12 h. | 1,3-dimethylbutyl hexadecyl ether 115 g (0.35 mol), 95% |
| | A-11 | tetradecyl alcohol 80 g (0.37 mol) | 4-methyl-2-pentanone 150 g (1.5 mol) | 5% Pd—C (pH 4.0) 1.6 g | While azeotropic dehydration $H_2$ pressure: 20 kg/cm² 150° C., 10 h. | 1,3-dimethylbutyl tetradecyl ether 104 g (0.35 mol), 94% |

TABLE A-3-continued

| | | Hydroxy compound | Carbonyl compound | Catalyst | Reaction condition | Product and Isolation yield |
|---|---|---|---|---|---|---|
| | A-12 | dodecyl alcohol 46.5 g (0.25 mol) | octyl aldehyde 128 g (1.0 mol) | 5% Pd—C (pH 6.6) 0.9 g | While azeotropic dehydration $H_2$ pressure: 20 kg/cm$^2$ 150° C., 8 h. | dodecyloctyl ether 68 g (0.23 mol), 92% |
| | A-13 | polyoxyethylene (p = 9.3) monododecyl ether* 107 g (0.18 mol) | octyl aldehyde 90 g (0.7 mol) | 5% Pd—C (pH 6.6) 2.1 g | While azeotropic dehydration $H_2$ pressure: 20 kg/cm$^2$ 150° C., 8 h. | polyoxyethylene(p = 9.3) dodecyloctyl ether 115 g (0.16 mol), 90% |

*p means an average addition molar number of ethyleneoxide.

TABLE A-4

| | | Hydroxy compound | Carbonyl compound | Catalyst | Reaction condition | Product and Isolation yield |
|---|---|---|---|---|---|---|
| Comp. Ex. | A-9 | tetradecyl alcohol 80 g (0.37 mol) | 4-methyl-2-pentanone 150 g (1.5 mol) | 5% Pd—C (pH 4.0) 1.6 g | $H_2$ press.: 100 kg/cm$^2$ 150° C., 15 h. | 1,3-dimethylbutyl tetradecyl ether 86 g (0.29 mol), 78% |
| | A-10 | hexadecyl alcohol 90 g (0.37 mol) | 4-methyl-2-pentanone 150 g (1.5 mol) | 5% Pd—C (pH 4.0) 1.8 g | $H_2$ press.: 20 kg/cm$^2$ 150° C., 12 h. | 1,3-dimethylbutyl hexadecyl ether 75 g (0.23 mol), 62% |
| | A-11 | tetradecyl alcohol 80 g (0.37 mol) | 4-methyl-2-pentanone 150 g (1.5 mol) | 5% Pd—C (pH 4.0) 1.6 g | $H_2$ pressure: 20 kg/cm$^2$ 15° C., 10 h. | 1,3-dimethylbutyl tetradecyl ether 67 g (0.22 mol), 61% |
| | A-12 | dodecyl alcohol 46.5 g (0.25 mol) | octyl aldehyde 128 g (1.0 mol) | 5% Pd—C (pH 6.6) 0.9 g | $H_2$ pressure: 20 kg/cm$^2$ 150° C., 8 h. | dodecyloctyl ether 45 g (0.15 mol), 60% |
| | A-13 | polyoxyethylene (p = 9.3) monododecyl ether* 107 g (0.18 mol) | octyl aldehyde 90 g (0.7 mol) | 5% Pd—C (pH 6.6) 2.1 g | $H_2$ pressure: 20 kg/cm$^2$ 150° C., 8 h. | polyoxyethylene(p = 9.3) dodecyloctyl ether 63 g (0.09 mol), 49% |

*p means an average addition molar number of ethyleneoxide.

Example A-14

Production of 1,3-dimethyl butyl tetradecyl ether

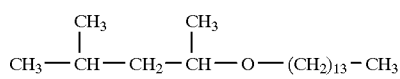

53.5 g (0.25 mol) of tetradecyl alcohol, 100 g (1.0 mol) of 4-methyl-2-pentanone, and 1.1 g of 5% Pd—C (pH 6.6) as a catalyst were charged into a 500 ml autoclave equipped with a hydrogen gas-introducing tube and a stirrer, and the contents were stirred at 20 kg/cm$^2$ of hydrogen pressure while introducing 0.2 liter/min of hydrogen gas to flow continuously at 150° C. for 8 hours.

After completion of the reaction, the catalyst was removed by filtration, and excess 4-methyl-2-pentanone was removed under reduced pressure. Further, distillation under reduced pressure (143° C./1 Torr) was carried out to obtain 71 g (0.24 mol) of intended 1,3-dimethyl butyl tetradecyl ether as a colorless and transparent liquid.

The isolation yield was 95%.

Comparative Example A-14

The reaction was carried out in the same manner as that in Example A-14, except that hydrogen was not caused to flow continuously, whereby 45 g (0.15 mol) of 1,3-dimethyl butyl tetradecyl ether was obtained as a colorless, transparent liquid.

The isolation yield was 60%.

Examples A'-15 to 25

The hydroxy compounds and the carbonyl compounds shown in Tables A'-5 and A'-6 were reacted in the presence of the catalysts shown in Tables A'-5 and A'-6 in the same manner as that in Example A-14, except that the reaction conditions were changed as shown in Tables A'-5 and A'-6.

The resulting products and the isolation yields thereof are shown in Tables A'-5 and A'-6 together with the results of Example A-14.

Comparative Examples A'-15 to 25

The hydroxy compounds and the carbonyl compounds shown in Tables A'-7 and A'-8 were reacted in the presence of the catalysts shown in Tables A'-7 and A'-8 in the same manner as that in Comparative Example A-14, except that the reaction conditions were changed as shown in Tables A'-7 and A'-8.

The resulting products and the isolation yields thereof are shown in Tables A'-7 and A'-8 together with the results of Comparative Example 14.

TABLE A'-5

|     |      | Hydroxy compound | Carbonyl compound | Catalyst | Reaction condition | Product and Isolation yield |
| --- | ---- | ---------------- | ----------------- | -------- | ------------------ | --------------------------- |
| Ex. | A-14 | tetradecyl alcohol 53.5 (0.25 mol) | 4-methyl-2-pentanone 100 g (1.0 mol) | 5% Pd—C (pH 6.6) 1.1 g | $H_2$ press.: 20 kg/cm$^2$ $H_2$ flow amount: 200 ml/min 150° C., 8 h. | 1,3-dimethylbutyl tetradecyl ether 71 g (0.24 mol), 95% |
|     | A'-15 | hexadecyl alcohol 60.5 g (0.25 mol) | 4-methyl-2-pentanone 100 g (1.0 mol) | 5% Pd—C (pH 7.1) 1.2 g | $H_2$ press.: 20 kg/cm$^2$ $H_2$ flow amount: 200 ml/min 150° C., 8 h. | 1,3-dimethylbutyl hexadecyl ether 78 g (0.24 mol), 96% |
|     | A'-16 | hexadecyl alcohol 24.2 g (0.1 mol) | 4-methyl-2-pentanone 100 g (1.0 mol) | 5% Pd—C (pH 6.6) 0.5 g | $H_2$ press.: 20 kg/cm$^2$ $H_2$ flow amount: 200 ml/min 150° C., 6 h. | 1,3-dimethylbutyl hexadecyl ether 31 g (0.095 mol), 95% |
|     | A'-17 | dodecyl alcohol 46.5 g (0.25 mol) | octylaldehyde 128 g (1.0 mol) | 5% Pd—C (pH 6.6) 0.9 g | Flow $H_2$ gas under atmospheric pressure $H_2$ flow amount: 200 ml/min 105° C., 8 h. | dodecyloctyl ether 73 g (0.245 mol), 98% |
|     | A'-18 | polyoxyethylene (p = 9.3) monododecyl ether* 107 g (0.18 mol) | cyclohexanone 70 g (0.71 mol) | 5% Pd—C (pH 7.1) 2.1 g | $H_2$ press.: 20 kg/cm$^2$ $H_2$ flow amount: 200 ml/min 150° C., 8 h. | polyoxyethylene(p = 9.3) cyclohexyl dodecyl ether 108 g (0.16 mol), 89% |
|     | A'-19 | polyoxyethylene (p = 9.3) monododecyl ether* 107 g (0.18 mol) | octylaldehyde 90 g (0.7 mol) | 5% Pd—C (pH 4.0) 2.1 g | $H_2$ press.: 20 kg/cm$^2$ $H_2$ flow amount: 200 ml/min 150° C., 8 h. | polyoxyethylene(p = 9.3) dodecyloctyl ether 115 g (0.16 mol), 90% |

*p means an average addition molar number of ethyleneoxide.

TABLE A'-6

|     |      | Hydroxy compound | Carbonyl compound | Catalyst | Reaction condition | Product and Isolation yield |
| --- | ---- | ---------------- | ----------------- | -------- | ------------------ | --------------------------- |
| Ex. | A'-20 | hexadecyl alcohol 60.5 g (0.25 mol) | 4-methyl-2-pentanone 100 g (1.0 mol) | 5% Pd—C (pH 7.1) 3.6 g | Flow $H_2$ gas under atmospheric press. $H_2$ flow amount: 300 ml/min 105° C., 7 h. | 1,3-dimethylbutyl hexadecyl ether 80.7 g (0.248 mol), 99% |
|     | A'-21 | hexadecyl alcohol 60.5 g (0.25 mol) | 4-methyl-2-pentanone 100 g (1.0 mol) | 5% Pd—C (pH 7.1) 3.6 g | $H_2$ press.: 1.5 kg/cm$^2$ $H_2$ flow amount: 300 ml/min 150° C.. 5 h. | 1,3-dimethylbutyl hexadecyl ether 80.7 g (0.248 mol), 99% |
|     | A'-22 | hexadecyl alcohol 60.5 g (0.25 mol) | 4-methyl-2-pentanone 100 g (1.0 mol) | 5% Pd—C (pH 7.1) 3.6 g | $H_2$ press.: 3 kg/cm$^2$ $H_2$ flow amount: 200 ml/min 150° C., 4 h. | 1,3-dimethylbutyl hexadecyl ether 80.7 g (0.248 mol), 99% |
|     | A'-23 | polyoxyethylene(p = 9.3) monododecyl ether* 107 g (0.18 mol) | octylaldehyde 92 g (0.72 mol) | 5% Pd—C (pH 7.1) 8.6 g | $H_2$ press.: 2 kg/cm$^2$ $H_2$ flow amount: 300 ml/min 120° C., 6 h. | polyoxyethylene(p = 9.3) dodecyloctyl ether 126 g (0.178 mol), 99% |
|     | A'-24 | diethyleneglycol monoisopropyl ether 51.8 g (0.35 mol) | methylethyl ketone 126 g (1.75 mol) | 5% Pd—C (pH 6.6) 2.1 g | $H_2$ press.: 2 kg/cm$^2$ $H_2$ flow amount: 200 ml/min 130° C., 6 h. | diethyleneglycol isopropyl (1-methylpropyl)ether 70.0 g (0.343 mol), 98% |
|     | A'-25 | dipropyleneglycol monopropyl ether 61.6 g (0.35 mol) | isobutyl-aldehyde 126 g (1.75 mol) | 5% Pd—C (pH 7.3) 2.5 g | $H_2$ press.: 3 kg/cm$^2$ $H_2$ flow amount: 200 ml/min 130° C., 5 h. | dipropyleneglycolpropyl (2-methylpropyl)ether 79.6 g (0.343 mol), 98% |

*p means an average addition molar number of ethyleneoxide.

TABLE A'-7

|     |      | Hydroxy compound | Carbonyl compound | Catalyst | Reaction condition | Product and Isolation yield |
| --- | ---- | ---------------- | ----------------- | -------- | ------------------ | --------------------------- |
| Comp. Ex. | A-14 | tetradecyl alcohol 53.5 (0.25 mol) | 4-methyl-2-pentanone 100 g (1.0 mol) | 5% Pd—C (pH 6.6) 1.6 g | $H_2$ press.: 20 kg/cm$^2$ 150° C., 8 h. | 1,3-dimethylbutyl tetradecyl ether 45 g (0.15 mol), 60% |
|     | A'-15 | hexadecyl alcohol 60.5 g (0.25 mol) | 4-methyl-2-pentanone 100 g (1.0 mol) | 5% Pd—C (pH 7.1) 1.2 g | $H_2$ press.: 20 kg/cm$^2$ 150° C., 8 h. | 1,3-dimethylbutyl hexadecyl ether 49 g (0.15 mol), 60% |
|     | A'-16 | hexadecyl alcohol 24.2 g (0.1 mol) | 4-methyl-2-pentanone 100 g (1.0 mol) | 5% Pd—C (pH 6.6) 0.5 g | $H_2$ press.: 20 kg/cm$^2$ 150° C., 6 h. | 1,3-dimethylbutyl hexadecyl ether 19 g (0.058 mol), 58% |
|     | A'-17 | dodecyl alcohol 46.5 g (0.25 mol) | octylaldehyde 128 g (1.0 mol) | 5% Pd—C (pH 6.6) 0.9 g | $H_2$ press.: atmospheric pressure 105° C., 8 h. | dodecyloctyl ether 4.5 g (0.915 mol), 6% |

TABLE A'-7-continued

|   | Hydroxy compound | Carbonyl compound | Catalyst | Reaction condition | Product and Isolation yield |
|---|---|---|---|---|---|
| A'-18 | polyoxyethylene (p = 9.3) monododecyl ether* 107 g (0.18 mol) | cyclohexanone 70 g (0.71 mol) | 5% Pd—C (pH 7.1) 2.1 g | $H_2$ press.: 20 kg/cm$^2$ 150° C., 8 h. | polyoxyethylene(p =9.3) cyclohexyl dodecyl ether 55 g (0.08 mol), 45% |
| A'-19 | polyoxyethylene (p = 9.3) monododecyl ether* 107 g (0.18 mol) | octylaldehyde 90 g (0.7 mol) | 5% Pd—C (pH 4.0) 2.1 g | $H_2$ press.: 20 kg/cm$^2$ 150° C., 8 h. | polyoxyethylene(p = 9.3) dodecyloctyl ether 63 g (0.09 mol), 49% |

*p means an average addition molar number of ethyleneoxide.

TABLE A'-8

|  |  | Hydroxy compound | Carbonyl compound | Catalyst | Reaction condition | Product and Isolation yield |
|---|---|---|---|---|---|---|
| Comp. Ex. | A'-20 | hexadecyl alcohol 60.5 (0.25 mol) | 4-methyl-2-pentanone 100 g (1.0 mol) | 5% Pd—C (pH 7.1) 3.6 g | $H_2$ press.: 1 kg/cm$^2$ 105° C., 7 h. | 1,3-dimethylbutyl hexadecyl ether 1.63 g (0.005 mol), 2% |
|  | A'-21 | hexadecyl alcohol 60.5 g (0.25 mol) | 4-methyl-2-pentanone 100 g (1.0 mol) | 5% Pd—C (pH 7.1) 3.6 g | $H_2$ press.: 1.5 kg/cm$^2$ 150° C., 5 h. | 1,3-dimethylbutyl hexadecyl ether 14.7 g (0.045 mol), 18% |
|  | A'-22 | hexadecyl alcohol 60.5 g (0.25 mol) | 4-methyl-2-pentanone 100 g (1.0 mol) | 5% Pd—C (pH 7.1) 3.6 g | $H_2$ press.: 3 kg/cm$^2$ 150° C., 4 h. | 1,3-dimethylbutyl hexadecyl ether 24.5 g (0.075 mol), 30% |
|  | A'-23 | polyoxyethylene (p = 9.3)monododecyl ether* 107 g (0.18 mol) | octylaldehyde 92 g (0.72 mol) | 5% Pd—C (pH 7.1) 8.6 g | $H_2$ press.: 2 kg/cm$^2$ 120° C., 6 h. | polyoxyethylene(p = 9.3) dodecyloctyl ether 3.82 g (0.0054 mol), 3% |
|  | A'-24 | diethyleneglycol monoisopropyl ether 51.8 g (0.35 mol) | methylethyl ketone 126 g (1.75 mol) | 5% Pd—C (pH 6.6) 2.1 g | $H_2$ press.: 2 kg/cm$^2$ 130° C., 6 h. | diethyleneglycol isopropyl(1-methylpropyl)ether 8.57 g (0.042 mol), 12% |
|  | A'-25 | dipropyleneglycol monopropyl ether 61.6 g (0.35 mol) | isobutyl-aldehyde 126 g (1.75 mol) | 5% Pd—C (pH 7.3) 2.5 g | $H_2$ press.: 3 kg/cm$^2$ 130° C., 5 h. | dipropyleneglycolpropyl (2-methylpropyl)ether 7.32 g (0.032 mol), 9% |

*p means an average addition molar number of ethyleneoxide.

Example A'-26

Production of 1,3-dimethyl butyl tetradecyl ether

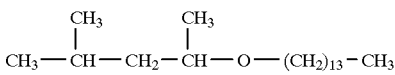

53.5 g (0.25 mol) of tetradecyl alcohol, 100 g (1.0 mol) of 4-methyl-2-pentanone and 1.6 g of 5% Pd—C (pH 6.6) as a catalyst were charged into a 500 ml autoclave equipped with a hydrogen gas-introducing tube, a stirrer and a dehydration-refluxing tube, and the contents were stirred at 8 kg/cm$^2$ of hydrogen pressure while introducing 700 ml/min of hydrogen gas to flow continuously at 150° C. for 7 hours. Water by-produced by the reaction was removed out of the system, and 4-methyl-2-pentanone which came out of the system together with the water was refluxed in the system.

After completion of the reaction, the catalyst was removed by filtration, and excess 4-methyl-2-pentanone was removed under reduced pressure. Further, distillation under reduced pressure (143° C./1 Torr) was carried out to obtain 73.8 g (0.248 mol) of intended 1,3-dimethylbutyl tetradecyl ether as a colorless and transparent liquid.

The isolation yield was 99%.

Comparative Example A'-26

The reaction was carried out in the same manner as that in Example A'-26, except that the dehydration-refluxing tube was not equipped, and hydrogen gas was not introduced to flow continuously, whereby 21.6 g (0.073 mol) of 1,3-dimethyl butyl tetradecyl ether was obtained as a colorless and transparent liquid.

The isolation yield was 29%.

Examples A'-27 to 37

The hydroxy compounds and the carbonyl compounds shown in Tables A'-9 and 10 were reacted in the presence of the catalysts shown in Tables A'-9 and 10 in the same manner as that in Example A'-26, except that the reaction conditions were changed as shown in Tables A'-9 and 10.

The resulting products and the isolation yields thereof are shown in Tables A'-9 and 10 together with the results of Comparative Example A'-26.

Comparative Example A'-27 to 37

The hydroxy compounds and the carbonyl compounds shown in Tables A'-11 and A'-12 were reacted in the presence of the catalysts shown in Tables A'-11 and A'-12 in the same manner as that in Comparative Example A'-26, except that the reaction conditions were changed as shown in Tables A'-11 and A'-12.

The resulting products and the isolation yields thereof are shown in Tables A'-11 and A'-12 together with the results of Comparative Example A'-26.

TABLE A'-9

|   |   | Hydroxy compound | Carbonyl compound | Catalyst | Reaction condition | Product and Isolation yield |
|---|---|---|---|---|---|---|
| Ex. | A'-26 | tetradecyl alcohol 53.5 g (0.25 mol) | 4-methyl-2-pentanone 100 g (1.0 mol) | 5% Pd—C (pH 6.6) 1.6 g | $H_2$ press.: 2 kg/cm$^2$ $H_2$ flow amount: 300 ml/min 150° C., 7 h. | 1,3-dimethylbutyl tetradecyl ether 73.8 g (0.248 mol), 99% |
|  | A'-27 | hexadecyl alcohol 60.5 g (0.25 mol) | 4-methyl-2-pentanone 100 g (1.0 mol) | 5% Pd—C (pH 7.1) 1.8 g | $H_2$ press.: 1.5 kg/cm$^2$ $H_2$ flow amount: 300 ml/min 150° C., 7 h. | 1,3-dimethylbutyl hexadecyl ether 79.9 g (0.245 mol), 98% |
|  | A'-28 | hexadecyl alcohol 60.5 g (0.25 mol) | 4-methyl-2-pentanone 100 (1.0 mol) | 5% Pd—C (pH 6.6) 3.6 g | Flow $H_2$ under atmospheric press. $H_2$ flow amount: 200 ml/min 105° C., 10 h. | 1,3-dimethylbutyl hexadecyl ether 73.8 g (0.248 mol), 99% |
|  | A'-29 | dodecyl alcohol 46.5 g (0.25 mol) | butylaldehyde 72 g (1.0 mol) | 5% Pd—C (pH 6.6) 1.4 g | $H_2$ press.: 1.5 kg/cm$^2$ $H_2$ flow amount: 200 ml/min 105° C, 6 h. | dodecylbutyl ether 58.9 g (0.248 mol), 99% |
|  | A'-30 | polyoxyethylene (p = 9.3) monododecyl ether* 107 g (0.18 mol) | cyclohexanone 70 g (0.71 mol) | 5% Pd—C (pH 7.1) 4.3 g | $H_2$ press.: 5 kg/cm$^2$ $H_2$ flow amount: 200 ml/min 150° C., 8 h. | polyoxyethylene(p = 9.3) cyclohexyl dodecyl ether 121 g (0.178 mol), 99% |
|  | A'-31 | polyoxyethylene (p = 9.3) monododecyl ether* 107 g (0.18 mol) | methylethyl ketone 50 g (0.7 mol) | 5% Pd—C (pH 4.0) 4.3 g | $H_2$ press.: 3 kg/cm$^2$ $H_2$ flow amount: 300 ml/min 150° C., 8 h. | polyoxyethylene(p = 9.3) dodecyl(1-methylpropyl) ether 116 g (0.178 mol), 99% |

*p means an average addition molar number of ethyleneoxide.

TABLE A'-10

|   |   | Hydroxy compound | Carbonyl compound | Catalyst | Reaction condition | Product and Isolation yield |
|---|---|---|---|---|---|---|
| Ex. | A'-32 | 2-hexadecyleicosyl alcohol 104 g (0.2 mol) | methylethyl ketone 72 g (1.0 mol) | 5% Pd—C (pH 7.3) 3.1 g | $H_2$ press.: 1.5 kg/cm$^2$ $H_2$ flow amount: 200 ml/min 150° C., 7 h. | 1-methylpropyl (2-hexadecyleicosyl) ether 114 g (0.198 mol), 99% |
|  | A'-33 | diethyleneglycol monoisopropyl ether 51.8 g (0.35 mol) | methylethyl ketone 126 g (1.75 mol) | 5% Pd—C (pH 6.6) 2.1 g | $H_2$ press.: 2 kg/cm$^2$ $H_2$ flow amount: 200 ml/min 130° C., 8 h. | diethyleneglycol isopropyl (1-methylpropyl)ether 69.3 g (0.34 mol), 97% |
|  | A'-34 | dipropyleneglycol monopropyl ether 61.6 g (0.35 mol) | isobutyl-aldehyde 126 g (1.75 mol) | 5% Pd—C (pH 7.3) 2.5 g | $H_2$ press.: 3 kg/cm$^2$ $H_2$ flow amount: 200 ml/min 130° C., 8 h. | dipropyleneglycol propyl (2-methylpropyl)ether 78.0 g (0.336 mol), 96% |
|  | A'-35 | 2-octanol 52.0 g (0.4 mol) | isobutyl-aldehyde 144 g (2.0 mol) | 5% Pd—C (pH 4.0) 2.1 g | $H_2$ press.: 1.5 kg/cm$^2$ $H_2$ flow amount: 200 ml/min 150° C., 8 h. | 1-methylheptyl (2-methylpropyl)ether 71.4 g (0.384 mol), 96% |
|  | A'-36 | polyoxyethylene (p = 9.3) monododecyl ether* 107 g (0.18 mol) | 4-methyl-2-pentanone 72 g (0.72 mol) | 5% Pd—C (pH 7.1) 8.6 g | Flow $H_2$ gas under atmospheric press. $H_2$ flow amount: 300 ml/min 150° C., 10 h. | polyoxyethylene(p = 9.3) dodecyl(1,3-dimethylbutyl)ether 120 g (0.176 mol), 98% |
|  | A'-37 | polyoxyethylene (p = 9.3) monododecyl ether* 107 g (0.18 mol) | octylaldehyde 92 g (0.72 mol) | 5% Pd—C (pH 7.1) 8.6 g | Flow $H_2$ gas under atmospheric press. $H_2$ flow amount: 300 ml/min 105° C., 8 h. | polyoxyethylene(p = 9.3) dodecyloctylether 126 g (0.178 mol), 99% |

*p means an average addition molar number of ethyleneoxide.

TABLE A'-11

|   |   | Hydroxy compound | Carbonyl compound | Catalyst | Reaction condition | Product and Isolation yield |
|---|---|---|---|---|---|---|
| Comp. Ex. | A'-26 | tetradecyl alcohol 53.5 g (0.25 mol) | 4-methyl-2-pentanone 100 g (1.0 mol) | 5% Pd—C (pH 6.6) 1.6 g | $H_2$ press.: 2 kg/cm$^2$ 150° C., 7 h. | 1,3 dimethylbutyl tetradecyl ether 21.6 g (0.073 mol), 29% |
|  | A'-27 | hexadecyl alcohol 60.5 g (0.25 mol) | 4-methyl-2-pentanone 100 g (1.0 mol) | 5% Pd—C (pH 7.1) 1.8 g | $H_2$ press.: 1.5 kg/cm$^2$ 150° C., 7 h. | 1,3-dimethylbutyl hexadecyl ether 25.3 g (0.078 mol), 31% |
|  | A'-28 | hexadecyl alcohol 60.5 g (0.25 mol) | 4-methyl-2-pentanone 100 g (1.0 mol) | 5% Pd—C (pH 6.6) 3.6 g | $H_2$ press.: 1 kg/cm$^2$ 105° C., 10 h. | 1,3-dimethylbutyl hexadecyl ether 9.78 g (0.030 mol), 12% |
|  | A'-29 | dodecyl alcohol 46.5 g (0.25 mol) | butylaldehyde 72 g (1.0 mol) | 5% Pd—C (pH 6.6) 1.4 g | $H_2$ press.: 1.5 kg/cm$^2$ 150° C., 6 h. | dodecylbutyl ether 20.6 g (0.085 mol), 34% |

TABLE A'-11-continued

| | Hydroxy compound | Carbonyl compound | Catalyst | Reaction condition | Product and Isolation yield |
|---|---|---|---|---|---|
| A'-30 | polyoxyethylene (p = 9.3) monododecyl ether* 107 g (0.18 mol) | cyclohexanone 70 g (0.71 mol) | 5% Pd—C (pH 7.1) 4.3 g | $H_2$ press.: 5 kg/cm$^2$ 150° C., 8 h. | polyoxyethylene(p = 9.3) cyclohexyl dodecyl ether 26.9 g (0.040 mol), 22% |
| A'-31 | polyoxyethylene (p = 9.3) monododecyl ether* 107 g (0.18 mol) | methylethyl ketone 50 g (0.7 mol) | 5% Pd—C (pH 4.0) 4.3 g | $H_2$ press.: 3 kg/cm$^2$ 150° C., 8 h. | polyoxyethylene(p = 9.3) dodecyl(1-methylpropyl) ether 29.3 g (0.045 mol), 25% |

*p means an average addition molar number of ethyleneoxide.

TABLE A'-12

| | | Hydroxy compound | Carbonyl compound | Catalyst | Reaction condition | Product and Isolation yield |
|---|---|---|---|---|---|---|
| Comp. Ex. | A'-32 | 2-hexadecyleicosyl alcohol 104 g (0.2 mol) | methylethyl ketone 72 g (1.0 mol) | 5% Pd—C (pH 7.3) 3.1 g | $H_2$ press.: 1.5 kg/cm$^2$ 150° C., 7 h. | 1-methylpropyl (2-hexadecyleicosyl)ether 25.4 g (0.044 mol), 22% |
| | A'-33 | diethyleneglycol monoisopropyl ether 52 g (0.35 mol) | methylethyl ketone 126 g (1.75 mol) | 5% Pd—C (pH 6.6) 2.1 g | $H_2$ press.: 2 kg/cm$^2$ 130° C., 8 h. | diethyleneglycol isopropyl(3-methylpropyl)ether 12.1 g (0.060 mol), 17% |
| | A'-34 | dipropyleneglycol monopropyl ether 62 g (0.35 mol) | isobutyl-aldehyde 126 g (1.75 mol) | 5% Pd—C (pH 7.3) 2.5 g | $H_2$ press.: 3 kg/cm$^2$ 130° C., 8 h. | dipropyleneglycol propyl(2-methylpropyl)ether 10.6 g (0.046 mol), 13% |
| | A'-35 | 2-octanol 52 g (0.4 mol) | isobutyl-aldehyde 144 g (2.0 mol) | 5% Pd—C (pH 4.0) 2.1 g | $H_2$ press.: 1.5 kg/cm$^2$ 150° C., 8 h. | 1-methylheptyl (2-methylpropyl)ether 11.9 g (0.064 mol), 16% |
| | A'-36 | polyoxyethylene (p =9.3) monododecyl 107 g (0.18 mol) | 4-methyl-2-pentanone 72 g (0.72 mol) | 5% Pd—C (pH 7.1) 8.6 g | $H_2$ press.: 1 kg/cm$^2$ 105° C., 10 h. | polyoxyethylene(p = 9.3) dodecyl(1,3-dimethylbutyl)ether 8.6 g (0.013 mol), 7% |
| | A'-37 | polyoxyethylene (p = 9.3) monododecyl ether* 107 g (0.18 mol) | octylaldehyde 92 g (0.72 mol) | 5% Pd—C (pH 7.1) 8.6 g | atmospheric press. 105° C., 8 h. | polyoxyethylene(p = 9.3) dodecyloctylether 5.1 g (0.072 mol), 40% |

*p means an average addition molar number of ethyleneoxide.

Example B-8

Synthesis of didecyl ether

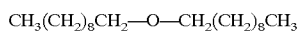

265 g (1.7 mol) of n-decylaldehyde, 5.3 g of 5% Pd—C (pH 6.6) as a catalyst and 2.7 g (0.02 mol) of anhydrous magnesium sulfate were charged into a 500 ml autoclave equipped with a hydrogen gas-introducing tube and a stirrer, and the contents were stirred at 100 kg/cm$^2$ of hydrogen pressure at 150° C. for 8 hours.

After completion of the reaction, the catalyst was removed by filtration. Further, distillation under reduced pressure (143° C./0.3 Torr) was carried out to obtain 228 g (0.77 mol) of intended didecyl ether as a colorless and transparent liquid.

The isolation yield was 90%.

Example B-9

Synthesis of bis(1,3-dimethylbutyl) ether

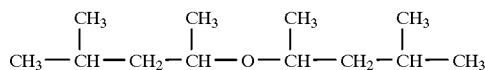

250 g (2.5 mol) of methyl isobutyl ketone, 5.0 g of 5% Pd—C (pH 3.8) as a catalyst and 2.5 g (0.02 mol) of anhydrous magnesium sulfate were charged into a 500 ml autoclave equipped with a hydrogen gas-introducing tube and a stirrer, and the contents were stirred at 150 kg/cm$^2$ of hydrogen pressure at 150° C. for 8 hours.

After completion of the reaction, the catalyst were removed by filtration. Further, distillation under reduced pressure (97° C./50 Torr) was carried out to obtain 174 g (0.94 mol) of intended bis(1,3-dimethylbutyl) ether as a colorless and transparent liquid.

The isolation yield was 75%.

Example B'-10

Synthesis of dibutyl ether

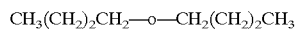

284 g (4.0 mol) of n-butylaldehyde and 8.5 g of 5% Pd—C (pH 6.6) as a catalyst were charged into a 500 ml autoclave equipped with a hydrogen gas-introducing tube, a stirrer and a cooling-dehydrating tube, and the contents were stirred at 60 kg/cm$^2$ of hydrogen pressure while introducing 700 ml/min of hydrogen gas to flow continuously at 150° C. for 8 hours to carry out the reaction while removing water by-produced by the reaction out of the system and n-butylaldehyde which came out of the system together with the water was returned again into the system.

After completion of the reaction, the catalyst was removed by filtration. Further, distillation (140° C./atmospheric pressure) was carried out to obtain 247 g (1.9 mol) of intended dibutyl ether as a colorless and transparent liquid.

The isolation yield was 95%.

Example B'-11

Synthesis of dihexyl ether

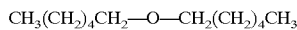

250 g (2.5 mol) of n-hexylaldehyde and 7.5 g of 5% Pd—C (pH 6.6) as a catalyst were charged into a 500 ml autoclave equipped with a hydrogen gas-introducing tube, a stirrer and a cooling-dehydrating tube, and the contents were stirred at 80 kg/cm² of hydrogen pressure while introducing 700 ml/min of hydrogen gas to flow continuously at 150° C. for 8 hours to carry out the reaction while removing water by-produced by the reaction out of the system and n-hexylaldehyde which came out of the system together with water was returned again into the system.

After completion of the reaction, the catalyst was removed by filtration. Further, distillation under reduced pressure (102° C./50 Torr) was carried out to obtain 216 g (1.16 mol) of intended dihexyl ether as a colorless and transparent liquid.

The isolation yield was 93%.

Example B'-12

Synthesis of dioctyl ether

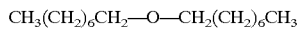

256 g (2.5 mol) of n-octylaldehyde and 7.7 g of 5% Pd—C (pH 3.8) as a catalyst were charged into a 500 ml autoclave equipped with a hydrogen gas-introducing tube, a stirrer and a cooling-dehydrating tube, and the contents were stirred at 100 kg/cm² of hydrogen pressure and 800 ml/min of hydrogen flow amount at 150° C. for 8 hours to carry out the reaction while removing water by-produced by the reaction out of the system and n-octylaldehyde which came out of the system together with water was returned again into the system.

After completion of the reaction, the catalyst was removed by filtration. Further, distillation under reduced pressure (127° C./3.5 Torr) was carried out to obtain 225 g (0.93 mol) of intended dioctyl ether as a colorless and transparent liquid.

The isolation yield was 93%.

Example B'-13

Synthesis of didecyl ether

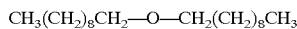

265 g (1.7 mol) of n-decylaldehyde and 8.0 g of 5% Pd—C (pH 6.6) as a catalyst were charged into a 500 ml autoclave equipped with a hydrogen gas-introducing tube, a stirrer and a cooling-dehydrating tube, and the contents were stirred at 100 kg/cm² of hydrogen pressure and 1 liter/min of hydrogen flow amount at 150° C. for 8 hours to carry out the reaction while removing water by-produced by the reaction out of the system and n-decylaldehyde which came out of the system together with water was returned again into the system.

After completion of the reaction, the catalyst was removed by filtration. Further, distillation under reduced pressure (142° C./0.3 Torr) was carried out to obtain intended didecyl ether of 233 g (0.78 mol) in the form of a colorless, transparent liquid.

The isolation yield was 92%.

Example B'-14

Synthesis of didodecyl ether

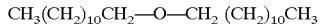

276 g (1.5 mol) of n-dodecylaldehyde and 8.3 g of 5% Pd—C (pH 3.8) as a catalyst were charged into a 500 ml autoclave equipped with a hydrogen gas-introducing tube, a stirrer and a cooling-dehydrating tube, and the contents were stirred at 120 kg/cm² of hydrogen pressure and 1 liter/min of hydrogen flow amount at 150° C. for 8 hours to carry out the reaction while removing water by-produced by the reaction out of the system and n-dodecylaldehyde which came out of the system together with the water was returned again into the system.

After completion of the reaction, the catalyst was removed by filtration. Further, distillation under reduced pressure (165° C./0.2 Torr) was carried out to obtain 247 g (0.70 mol) of intended didodecyl ether as a colorless and transparent liquid.

The isolation yield was 93%.

Example B'-15

Synthesis of bis(1,3-dimethylbutyl) ether

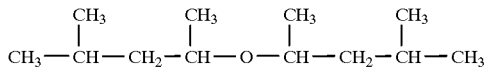

250 g (2.5 mol) of methyl isobutyl ketone and 10 g 5% Pd—C (pH 3.8) as a catalyst were charged into a 500 ml autoclave equipped with a hydrogen gas- introducing tube, a stirrer and a cooling-dehydrating tube, and the contents were stirred at 150 kg/cm² of hydrogen pressure and 700 ml/min of hydrogen flow amount at 150° C. for 8 hours to carry out the reaction while removing water by-produced by the reaction out of the system and methyl isobutyl ketone which came out of the system together with the water was returned again into the system.

After completion of the reaction, the catalyst was removed by filtration. Further, distillation under reduced pressure (97° C./50 Torr) was carried out to obtain 184 g (0.99 mol) of intended bis(1,3-dimethylbutyl) ether as a colorless and transparent liquid.

The isolation yield was 79%.

Example B'-16

Synthesis of dicyclohexyl ether

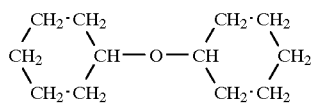

245 g (2.5 mol) of cyclohexanone and 9.8 g of 5% Pd—C (pH 6.6) as a catalyst were charged into a 500 ml autoclave equipped with a hydrogen gas-introducing tube, a stirrer and a cooling-dehydrating tube, and the contents were stirred at 150 kg/cm² of hydrogen pressure and 700 ml/min of hydrogen flow amount at 150° C. for 8 hours to carry out the reaction while removing water by-produced by the reaction out of the system and cyclohexanone which came out of the system together with the water was returned again into the system.

After completion of the reaction, the catalyst was removed by filtration. Further, refining was carried out with silica gel column chromatography, whereby 187 g (1.03 mol) of intended dicyclohexyl ether was obtained as a colorless and transparent liquid.

The isolation yield was 82%.

Example C-1

150 g (0.027 mol) of ethylene oxide adduct of dodecyl alcohol (ethylene oxide average addition molar number: 120 mol), 44 g (0.76 mol) of acetone, 0.94 g (7.84 milli mol) of anhydrous magnesium sulfate and 3 g of 5% Pd—C (pH 4.0) as a catalyst were charged into a 500 ml autoclave equipped with a hydrogen gas-introducing tube and a stirrer, and the reaction was carried out at 100 kg/cm$^2$ of hydrogen pressure at 150° C. for 8 hours. After completion of the reaction, the catalyst and magnesium sulfate were removed by filtration, and excess acetone was removed under reduced pressure, whereby 148 g of polyoxyethylene(ethylene oxide average addition molar number: 120 mol)-isopropyl-lauryl ether was obtained as a white solid matter (isolation yield: 98%).

Example C-2

200 g (0.03 mol) of ethylene oxide adduct of dodecyl alcohol (ethylene oxide average addition molar number: 150 mol), 50 g (0.86 mol) of acetone, 1.03 g (8.57 milli mol) of anhydrous magnesium sulfate and 4 g of 5% Pd—C (pH 4.0) as a catalyst were charged into a 500 ml autoclave equipped with a hydrogen gas-introducing tube and a stirrer, and the reaction was carried out at 100 kg/cm$^2$ of hydrogen pressure at 150° C. for 8 hours. After completion of the reaction, the catalyst and magnesium sulfate were removed by filtration, and excess acetone was removed under reduced pressure, whereby 199 g of polyoxyethylene(ethylene oxide average addition molar number: 150 mol)-isopropyl-lauryl ether was obtained as a white solid matter (isolation yield: 99%).

Example C-3

150 g (0.027 mol) of ethylene oxide adduct of dodecyl alcohol (ethylene oxide average addition molar number: 120 mol), 54 g (0.75 mol) of methyl ethyl ketone, 0.94 g (7.87 milli mol) of anhydrous magnesium sulfate and 3 g of 5% Pd—C (pH 4.0) as a catalyst were charged into a 500 ml autoclave equipped with a hydrogen gas-introducing tube and a stirrer, and the reaction was carried out at 100 kg/cm$^2$ of hydrogen pressure at 150° C. for 8 hours. After completion of the reaction, the catalyst and magnesium sulfate were removed by filtration, and excess methyl ethyl ketone was removed under reduced pressure, whereby 147 g of polyoxyethylene(ethylene oxide average addition molar number: 120 mol)-1-methylpropyl-lauryl ether was obtained as a white solid matter (isolation yield: 96%)

Example C-4

83 g (0.036 mol) of ethylene oxide and propylene oxide adduct of stearyl alcohol (ethylene oxide average addition molar number: 20 mol, propylene oxide average addition molar number: 20 mol), 53 g (0.93 mol) of acetone, 1.85 g (0.015 mol) of anhydrous magnesium sulfate and 1.7 g of 5% Pd—C (pH 4.0) as a catalyst were charged into a 500 ml autoclave equipped with a hydrogen gas-introducing tube and a stirrer and the reaction was carried out at 100 kg/cm$^2$ of hydrogen pressure at 150° C. for 10 hours. After completion of the reaction, the catalyst and magnesium sulfate were removed by filtration, and excess acetone was removed under reduced pressure, whereby 74 g of polyoxyalkylene (ethylene oxide average addition molar number: 20 mol, propylene oxide average addition molar number: 20 mol)-isopropyl-lauryl ether was obtained as a colorless and transparent liquid (isolation yield: 87%).

Example C-5

150 g (0.047 mol) of ethylene oxide and propylene oxide adduct of 2-octyl alcohol (ethylene oxide average addition molar number: 30 mol, propylene oxide average addition molar number: 30 mol), 150 g (1.5 mol) of methyl isobutyl ketone, 2.42 g (0.02 mol) of anhydrous magnesium sulfate and 3 g of 5% Pd—C (pH 4.0) as a catalyst were charged into a 500 me autoclave equipped with a hydrogen gas-introducing tube and a stirrer, and the reaction was carried out at 100 kg/cm$^2$ of hydrogen pressure at 150° C. for 10 hours. After completion of the reaction, the catalyst and magnesium sulfate were removed by filtration, and excess methyl isobutyl ketone was removed under reduced pressure, whereby 143 g of polyoxyalkylene(ethylene oxide average addition molar number: 30 mol, propylene oxide average addition molar number: 30 mol)-1,3-dimethylbutyl-1-methylheptyl ether was obtained as a colorless and transparent liquid (isolation yield: 93%).

Example C-6

150 g (0.047 mol) of ethylene oxide and propylene oxide adduct of 2-octyl alcohol (ethylene oxide average addition molar number: 30 mol, propylene oxide average addition molar number: 30 mol), 147 g (1.5 mol) of cyclohexanone, 2.42 g (0.02 mol) of anhydrous magnesium sulfate and 3 g of 5% Pd—C (pH 4.0) as a catalyst were charged into a 500 ml autoclave equipped with a hydrogen gas-introducing tube and a stirrer, and the reaction was carried out at 100 kg/cm$^2$ of hydrogen pressure at 150° C. for 10 hours. After completion of the reaction, the catalyst and magnesium sulfate were removed by filtration, and excess cyclohexanone was removed under reduced pressure, whereby 102 g of polyoxyalkylene(ethylene oxide average addition molar number: 30 mol, propylene oxide average addition molar number: 30 mol)-cyclohexyl-1-methylheptyl ether was obtained as a colorless and transparent liquid (isolation yield: 91%).

Example C'-7

164 g (0.05 mol) of ethylene oxide and propylene oxide adduct of dodecyl alcohol (ethylene oxide average addition molar number: 30 mol, propylene oxide average addition molar number: 30 mol), 150 g (1.5 mol) of methyl isobutyl ketone and 3 g of 5% Pd—C (pH 4.0) as a catalyst were charged into a 500 me autoclave equipped with a hydrogen gas-introducing tube and a stirrer, and the reaction was carried out at 10 kg/cm$^2$ of hydrogen pressure and 300 me/min of hydrogen gas flow amount at 105° C. for 10 hours. Water by-produced by the reaction was removed out of the system, and unreacted methyl isobutyl ketone which came out of the system together with the water was returned again into the system.

After completion of the reaction, the catalyst was removed by filtration, and excess methyl isobutyl ketone was removed under reduced pressure, whereby 158 g of polyoxyalkylene(ethylene oxide average addition molar number: 30 mol, propylene oxide average addition molar number: 30 mol)-1,3-dimethylbutyl-dodecyl ether was obtained as a colorless and transparent liquid (isolation yield: 95%).

Example C'-8

150 g (0.027 mol) of ethylene oxide adduct of dodecyl alcohol (ethylene oxide average addition molar number: 120 mol), 75 g (0.75 mol) of methyl isobutyl ketone and 10 g of 5% Pd—C (pH 4.0) as a catalyst were charged into a 500 ml autoclave equipped with a hydrogen gas-introducing tube and a stirrer, and the reaction was carried out at 10 kg/cm² of hydrogen pressure and 300 ml/min of hydrogen gas flow amount at 105° C. for 10 hours. Water by-produced by the reaction was removed out of the system, and unreacted methyl isobutyl ketone which came out of the system together with the water was returned again into the system.

After completion of the reaction, the catalyst was removed by filtration, and excess methyl isobutyl ketone was removed under reduced pressure, whereby 144 g of polyoxyalkylene(ethylene oxide average addition molar number: 120 mol)-1,3-dimethylbutyl-dodecyl ether was obtained as a white solid matter (isolation yield: 96%).

Example C'-9

150 g (0.027 mol) of ethylene oxide adduct of dodecyl alcohol (ethylene oxide average addition molar number: 120 mol), 54 g (0.75 mol) of isobutylaldehyde and 10 g of 5% Pd—C (pH 4.0) as a catalyst were charged into a 500 ml autoclave equipped with a hydrogen gas-introducing tube and a stirrer, and the reaction was carried out at 10 kg/cm² of hydrogen pressure and 300 ml/min of hydrogen gas flow amount at 80° C. for 10 hours. Water by-produced by the reaction was removed out of the system, and unreacted isobutylaldehyde which came out of the system together with water was returned again into the system.

After completion the reaction, the catalyst was removed by filtration, and excess isobutylaldehyde was removed under reduced pressure, whereby 143 g of polyoxyalkylene (ethylene oxide average addition molar number: 120 mol)-2-methylpropyl-dodecyl ether was obtained as a white solid matter (isolation yield: 96%).

Example C'-10

83 g (0.036 mol) of ethylene oxide and propylene oxide adduct of octadecyl alcohol (ethylene oxide average addition molar number: 20 mol, propylene oxide average addition molar number: 20 mol), 67 g (0.93 mol) of methyl ethyl ketone and 5 g of 5% Pd—C (pH 4.0) as a catalyst were charged into a 500 ml autoclave equipped with a hydrogen gas-introducing tube and a stirrer, and the reaction was carried out at 10 kg/cm² of hydrogen pressure and 300 ml/min of hydrogen gas flow amount at 80° C. for 10 hours. Water by-produced by the reaction was removed out of the system, and unreacted methyl ethyl ketone which came out of the system together with the water was returned again into the system.

After completion of the reaction, the catalyst was removed by filtration, and excess methyl ethyl ketone was removed under reduced pressure, whereby 81 g of polyoxyalkylene(ethylene oxide average addition molar number: 20 mol, propylene oxide average addition molar number: 20 mol)-1-methylpropyl-octadecyl ether was obtained as a colorless and transparent liquid (isolation yield: 95%).

Example C'-11

109 g (0.020 mol) of ethylene oxide adduct of dodecyl alcohol (ethylene oxide average addition molar number: 120 mol), 44 g (0.76 mol) of acetone and 8 g of 5% Pd—C (pH 4.0) as a catalyst were charged into a 500 ml autoclave equipped with a hydrogen gas-introducing tube and a stirrer, and the reaction was carried out at 10 kg/cm² of hydrogen pressure and 300 ml/min of hydrogen gas flow amount at 120° C. for 10 hours.

After completion of the reaction, the catalyst was removed by filtration, and excess acetone was removed under reduced pressure, whereby 107 g of polyoxyalkylene (ethylene oxide average addition molar number: 120 mol)-isopropyl-dodecyl ether was obtained as a white solid matter (isolation yield: 97%).

Example C'-12

83 g (0.036 mol) of ethylene oxide and propylene oxide adduct of octadecyl alcohol (ethylene oxide average addition molar number: 20 mol, propylene oxide average addition molar number: 20 mol), 67 g (0.93 mol) of isobutyl aldehyde and 5 g of 5% Pd—C (pH 4.0) as a catalyst were charged into a 500 ml autoclave equipped with a hydrogen gas-introducing tube and a stirrer, and the reaction was carried out at 10 kg/cm² of hydrogen pressure and 300 me/min hydrogen gas flow amount at 120° C. for 10 hours.

After completion of the reaction, the catalyst was removed by filtration, and excess isobutylaldehyde was removed under reduced pressure, whereby 82 g of polyoxyalkylene(ethylene oxide average addition molar number: 20 mol, propylene oxide average addition molar number: 20 mol)-2-methylpropyl-octadecyl ether was obtained as a colorless and transparent liquid (isolation yield: 96%).

Example D-1

Synthesis of 1,6-hexanediol diisopropyl ether

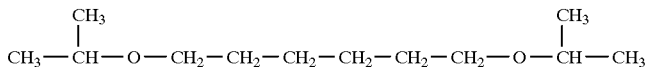

47 g (0.4 mol) of 1,6-hexanediol, 232 g (4 mol) of acetone, 0.94 g of 5% Pd—C (pH 6.4) as a catalyst and 28 g (0.23 mol) of anhydrous magnesium sulfate as a dehydrating agent were charged into a 500 ml autoclave equipped with a hydrogen gas-introducing tube and a stirrer, and the content were stirred at 70 kg/cm² of hydrogen pressure at 150° C. for 7 hours.

After completion of the reaction, the catalyst and magnesium sulfate were removed by filtration, and excess acetone was removed under reduced pressure. Further, refining with silica gel column chromatography was carried out to obtain 79 g (0.39 mol) of intended 1,6-hexanediol diisopropyl ether as a colorless and transparent liquid.

The isolation yield was 98% (based on 1,6-hexanediol).

Examples D-2 to 4

The polyhydric hydroxy compounds and the monovalent carbonyl compounds shown in Table D-1 were reacted in the presence of the catalysts and the dehydrating agents shown in Table D-1 in the same manner as that in Example D-1, except that the reaction conditions were changed as shown in Table D-1.

The resulting products and the isolation yields thereof are shown in Table D-1.

The isolation yields are based on the hydroxy compounds.

TABLE D-1

| | | Hydroxy compound | Carbonyl compound | Catalyst | Dehydrating agent | Reaction condition | Product and Isolation yield |
|---|---|---|---|---|---|---|---|
| Ex. | D-2 | 1,9-nonanediol 32 g (0.2 mol) | 4-methyl-2-pentanone 200 g (2.0 mol) | 5% Pd—C (pH 6.4) 0.64 g | anhydrous magnesium sulfate 13 g (0.11 mol) | $H_2$ pressure: 70 kg/cm$^2$ 150° C., 7 h. | 1,9-nonanediol bis(1,3-dimethylbutyl)ether 63 g (0.19 mol), 95% |
| | D-3 | 3-methyl-1,5-pentanediol 35 g (0.3 mol) | methylethyl ketone 216 g (3 mol) | 5% Pd—C (pH 7.1) 0.70 g | anhydrous magnesium sulfate 20 g (0.17 mol) | $H_2$ pressure: 100 kg/cm$^2$ 150° C., 7 h. | 3-methyl-1,5-pentanediol bis(1-methylpropyl)ether 66 g (0.29 mol), 96% |
| | D-4 | glycerol 28 g (0.3 mol) | acetone 261 g (4.5 mol) | 5% Pd—C (pH 7.1) 0.56 g | anhydrous magnesium sulfate 31 g (0.26 mol) | $H_2$ pressure: 100 kg/cm$^2$ 150° C., 15 h. | glycerolisopropylether tri- 1.3 g (0.006 mol), 2% di- 32 g (0.18 mol), 60% mono- 12 g (0.09 mol), 30% |

Examples D-5 to 9

The monohydric hydroxy compounds and the polyvalent carbonyl compounds shown in Table D-2 were reacted in the presence of the catalysts and the dehydrating agents shown in Table D-2 in the same manner as that in Example D-1, except that the reaction conditions were changed as shown in Table D-2.

The resulting products and the isolation yields thereof are shown in Table D-2.

The isolation yields are based on the carbonyl compounds.

TABLE D-2

| | | Hydroxy compound | Carbonyl compound | Catalyst | Dehydrating agent | Reaction condition | Product and Isolation yield |
|---|---|---|---|---|---|---|---|
| Ex. | D-5 | n-octyalcohol 260 g (2 mol) | 2,5-hexanedion 23 g (0.2 mol) | 5% Pd—C (pH 6.4) 0.46 g | anhydrous magnesium sulfate 13 g (0.11 mol) | $H_2$ pressure: 70 kg/cm$^2$ 150° C., 7 h. | 2,5-hexanediol dioctylether 67 g (0.196 mol), 98% |
| | D-6 | n-butylalcohol 222 g (3 mol) | 1,4-cyclohexanedion 34 g (0.3 mol) | 5% Pd—C (pH 6.4) 0.68 g | anhydrous magnesium sulfate 20 g (0.17 mol) | $H_2$ pressure: 70 kg/cm$^2$ 150° C., 6 h. | 1,4-cyclohexanediol dibutylether 65 g (0.285 mol), 95% |
| | D-7 | tetradecylalcohol 214 g (1 mol) | 1,4-cyclohexanedion 11 g (0.1 mol) | 5% Pd—C (pH 7.1) 0.44 g | anhydrous magnesium sulfate 7.2 g (0.06 mol) | $H_2$ pressure: 70 kg/cm$^2$ 150° C., 7 h. | 1,4-cyclohexanedion ditetradecylether 47 g (0.093 mol), 93% |
| | D-8 | diethyleneglycol monobutylether 243 g (1.5 mol) | 2,5-hexanedion 17 g (0.15 mol) | 5% Pd—C (pH 7.1) 0.68 g | anhydrous magnesium sulfate 11 g (0.09 mol) | $H_2$ pressure: 70 kg/cm$^2$ 150° C., 7 h. | 2,5-hexanediol bis(diethyleneglycol monobutylether)ether 58 g (0.143 mol), 95% |
| | D-9 | polyoxyethylene (p = 6.0) monododecyl ether* 225 g (0.5 mol) | 2,5-hexanedion 6.8 g (0.06 mol) | 5% Pd—C (pH 3.8) 0.27 g | anhydrous magnesium sulfate 6.0 g (0.05 mol) | $H_2$ pressure: 100 kg/cm$^2$ 150° C., 10 h. | 2,5-hexanediol bis{polyoxyethylene (p = 6.0) monododecylether}ether 53 g (0.054 mol), 90% |

*p means an average addition molar number of ethyleneoxide.

Example D-10

Synthesis of isopropylpolyoxyethylene(P=4.3)glycerol

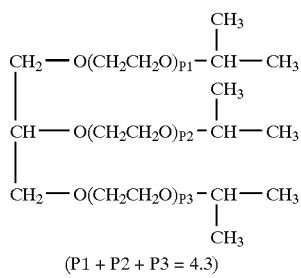

(P1 + P2 + P3 = 4.3)

99 g (0.15 mol) of polyoxyethylene(P=4.3)glycerol, 133 g (2.3 mol) of acetone, 2.0 g of 5% Pd—C (pH 3.8) as a catalyst and 16 g (0.13 mol) of anhydrous magnesium sulfate as a dehydrating agent were charged into a 500 ml autoclave equipped with a hydrogen gas-introducing tube and a stirrer, and the contents were stirred at 100 kg/cm$^2$ of hydrogen pressure at 150° C. for 10 hours.

After completion of the reaction, the catalyst and magnesium sulfate were removed by filtration, and excess acetone was removed under reduced pressure. Further, the low boiling portion were completely removed by steaming to obtain 100 g of intended isopropylpolyoxyethylene(P=4.3)glycerol as a colorless and transparent liquid.

The etherification rate calculated from the hydroxyl value [255 (KOH mg/g)] before the reaction and the hydroxyl value [26 (KOH mg/g)] after the reaction was 76%.

Example D-11

The polyhydric hydroxy compound and the monovalent carbonyl compound shown in Table D-3 were reacted in the presence of the catalyst and the dehydrating agent shown in Table D-3 in the same manner as that in Example D-10, except that the reaction conditions were changed as shown in Table D-3.

The resulting product and the etherification rate thereof are shown in Table D-3.

Example D-12

Synthesis of 1,4-butanediol bis(1,3-dimethylbutyl) ether

18 g (0.2 mol) of 1,4-butanediol, 200 g (2 mol) of methyl isobutyl ketone and 2 g of 5% Pd—C (pH 7.1) as a catalyst were charged into a 500 ml autoclave equipped with a hydrogen gas-introducing tube, a stirrer and a cooling-dehydrating tube, and the contents were stirred at 3 kg/cm$^2$ of hydrogen pressure and 300 me/min of hydrogen flow amount at 105° C. for 10 hours. Water by-produced by the reaction was removed out of the system, and unreacted methyl isobutyl ketone which came out of the system together with the water was put back into the system.

After completion of the reaction, the catalyst was removed by filtration, and excess methyl isobutyl ketone was removed under reduced pressure. Further, refining was carried out with silica gel column chromatography to obtain 50.6 g (0.196 mol) of intended 1,4-butanediol bis(1,3-dimethylbutyl) ether as a colorless and transparent liquid.

The isolation yield was 98% (based on 1,4-butanediol).

Examples D-13 to 15

The polyhydric hydroxy compounds and the monovalent carbonyl compounds shown in Table D-4 were reacted in the presence of the catalysts shown in Table D-4 in the same manner as that in Example D-12, except that the reaction conditions were changed as shown in Table D-4.

The resulting products and the isolation yields thereof are shown in Table D-4.

The isolation yields are based on the hydroxy compounds.

TABLE D-3

| | | Hydroxy compound | Carbonyl compound | Catalyst | Dehydrating agent | Reaction condition | Product and Isolation yield |
|---|---|---|---|---|---|---|---|
| Ex. | D-11 | polyethyleneglycol [average molecular wt.: 400] 80 g (0.2 mol) | acetone 139 g (2.4 mol) | 5% Pd—C (pH 6.4) 3.2 g | anhydrous magnesium sulfate 28 g (0.23 mol) | H$_2$ pressure: 70 kg/cm$^2$ 150° C., 12 h. | polyethyleneglycol diisopropylether 86 g. isopropyletherification rate (93%) |

TABLE D-4

| | | Hydroxy compound | Carbonyl compound | Catalyst | Reaction condition | Product and Isolation yield |
|---|---|---|---|---|---|---|
| Ex. | D-13 | 1,3-hexanediol 24 g (0.2 mol) | cyclohexane 157 g (1.6 mol) | 5% Pd—C (pH 7.1) 2 g | H$_2$ pressure: 5 kg/cm$^2$ H$_2$ flow amount: 400 ml/min 120° C. | 1,6-hexanediol dicyclohexylether 54.7 g (0.194 mol), 97% |
| | D-14 | triethyleneglycol 30 g (0.2 mol) | methylisobutyl ketone 200 g (2 mol) | 50% Pd—C (pH 7.1) 2.2 g | H$_2$ pressure: 3 kg/cm$^2$ H$_2$ flow amount: 300 ml/min 105° C. | triethyleneglycol bis(1,3-dimethylbutyl)ether 62.9 g (0.198 mol), 99% |
| | D-15 | 3-methyl-1,5-pentanediol 30 g (0.25 mol) | isobutyl-aldehyde 180 g (2.5 mol) | 5% Pd—C (pH 6.4) 2.2 g | H$_2$ pressure: 3 kg/cm$^2$ H$_2$ flow amount: 300 ml/min 105° C. | 3-methyl-1,5-pentanediol bis(2-methylpropyl)ether 56.9 g (0.248 mol), 99% |

Examples D-16 to 17

The monohydric hydroxy compounds and the polyvalent carbonyl compounds shown in Table D-5 were reacted in the presence of the catalysts shown in Table D-5 in the same manner as that in Example D-12, except that the reaction conditions were changed as shown in Table D-5.

The resulting products and the isolation yields thereof are shown in Table D-5.

The isolation yields are based on the carbonyl compounds.

TABLE D-5

|  |  | Hydroxy compound | Carbonyl compound | Catalyst | Reaction condition | Product and Isolation yield |
|---|---|---|---|---|---|---|
| Ex. | D-16 | octanol 208 g (1.6 mol) | 1,4-cyclo-hexanedion 22 g (0.2 mol) | 5% Pd—C (pH 7.1) 2 g | H$_2$ pressure: 5 kg/cm$^2$ H$_2$ flow amount: 400 ml/min 120° C. | 1,4-cyclohexanediol dioctylether 66.6 g (0.196 mol), 98% |
|  | D-17 | octanol 208 g (1.6 mol) | 2,5-hexanedion 23 g (0.2 mol) | 5% Pd—C (pH 6.4) 2 g | H$_2$ pressure: 5 kg/cm$^2$ H$_2$ flow amount: 400 ml/min 120° C. | 2,5-hexanediol dioctylether 66.3 g (0.194 mol), 97% |

Example D-18

Synthesis of 1,9-nonanedioldiisopropyl ether

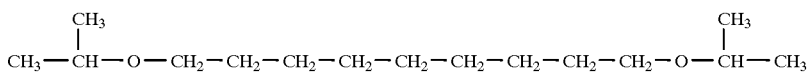

48 g (0.3 mol) of 1,9-nonanediol, 174 g (3 mol) of acetone and 4 g of 5% Pd—C (pH 7.1) 4 g as a catalyst were charged into a 500 ml autoclave equipped with a hydrogen gas-introducing tube and a stirrer, and the reaction was carried out at 10 kg/cm$^2$ of hydrogen pressure and 250 ml/min of hydrogen flow amount at 100° C. for 10 hours.

After completion of the reaction, the catalyst was removed by filtration, and excess acetone was removed under reduced pressure. Further, refining was carried out with silica gel column chromatography to obtain 72.5 g (0.297 mol) of intended 1,9-nonanedioldiisopropyl ether as a colorless and transparent liquid.

The isolation yield was 99% (based on 1,9-nonanediol).

Example D-19

Synthesis of triethylene glycol bis(2-methyl)propyl ether

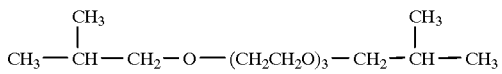

30 g (0.2 mol) of triethylene glycol, 144 g (2 mol) of isobutylaldehyde and 2.2 g of 5% Pd—C (pH 6.4) as a catalyst were charged into a 500 ml autoclave equipped with a hydrogen gas-introducing tube and a stirrer, and the reaction was carried out at 10 kg/cm$^2$ of hydrogen pressure and 250 ml/min of hydrogen flow amount at 110° C. for 10 hours.

After completion of the reaction, the catalyst was removed by filtration, and excess isobutylaldehyde was removed under reduced pressure. Further, refining was carried out with silica gel column chromatography to obtain 51.4 g (0.196 mol) of intended triethylene glycol bis(2-methyl)propyl ether as a colorless and transparent liquid.

The isolation yield was 98% (based on triethylene glycol).

Example D-20

106 g (0.9 mol) of 3-methyl-1,5-pentanediol, 101 g (0.9 mol) of 1,4-cyclohexanedione and 7 g of 5% Pd—C (pH 7.1) as a catalyst were charged into a 500 ml autoclave equipped with a hydrogen gas-introducing tube and a stirrer, and the reaction was carried out at 3 kg/cm$^2$ of hydrogen pressure and 300 ml/min of hydrogen flow amount at 100° C. for 10 hours.

After completion of the reaction, the catalyst was removed by filtration to obtain 180 g of the product. This product was determined by GPC (gel permeation chromatography), and the peaks of compounds having about 230 to 1500 of molecular weight were observed. The main peak is at about 345, and it has been found from the results obtained by IR and $^1$H-NMR that the resulting product is a mixture of compounds represented by the following formulae.

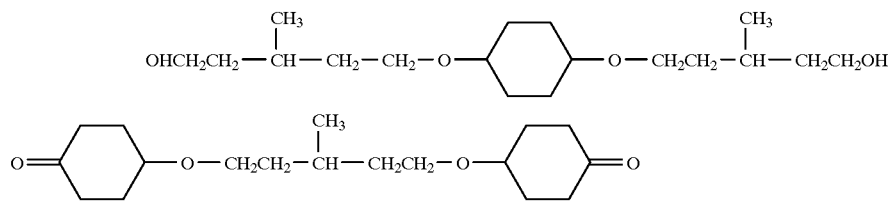

We claim:

1. A process for producing an ether compound, which comprises reacting a hydroxy compound with a carbonyl compound under a hydrogen gas atmosphere in the presence of a catalyst, while removing water produced by the reaction; and wherein said carbonyl compound is selected from the group consisting of aldehydes and ketones; and wherein a molar ratio of said hydroxy compound to said aldehydes or ketones used is from about 50/1 to 1/50.

2. The process of claim 1, in which the water is removed by at least one method selected from the group consisting of:

(1) being in the presence of a dehydrating agent;

(2) distillating off the water; and (3) blowing hydrogen gas to flow through the reaction system.

3. The process of claim 2, in which the dehydrating agent is selected from the group consisting of an inorganic salt, an oxide, a hydroxide, a crystalline zeolite and silica gel.

4. The process of claim 2, in which the amount of the dehydrating agent used is in the range of from 0.1 to 100 molar % based on the starting carbonyl compound.

5. The process of claim 2, in which the water is distilled off by azeotropic dehydration.

6. The process of claim 1, in which the hydroxy compound is represented by the following formula (1):

$$R_1-(OA)_n-OH \qquad (1)$$

wherein $R_1$ represents a straight or branched alkyl group having 3 to 24 carbon atoms, lower to up to 40 carbon alkenyl, or a cycloalkyl group having 3 to 12 carbon atoms; A represents an alkylene group having 2 to 12 carbon atoms, which may have a hydroxy group; two or more A's may be the same as or different from one another; and n is a number of 0 to 500.

7. The process of claim 1, in which the ketones or aldehydes have the formula (2):

(2)

wherein $R_2$ and $R_3$ represent, independently of each other, a hydrogen atom or a straight or branched alkyl group having 1 to 20 carbon atoms or lower to up to 20 carbon alkenyl; or $R_2$ and $R_3$ together constitute a cyclic structure.

8. The process of claim 1, wherein the catalyst is a palladium catalyst supported on carbon, alumina, silica or silica-alumina.

9. The process of claim 1, wherein said molar ratio of said hydroxy compound to said aldehydes or ketones used is from about 10/1 to 1/10.

10. The process of claim 1, wherein said hydroxy compound is selected from the group consisting of a diol having from 2 to 20 carbon atoms, glycerol, trimethylol ethane, trimethylol propane, pentaerythritol, saccharide and alkylene oxide adducts.

11. A process for producing an ether compound, which comprises reacting (a) a hydroxy compound with a carbonyl compound or (b) a carbonyl compound, under a hydrogen gas atmosphere at a pressure of up to 20 kg/cm² in the presence of a catalyst, while removing water produced by the reaction.

12. The process of claim 11, in which the water is removed by at least one method selected from the group consisting of:

(1) being in the presence of a dehydrating agent;

(2) distillating off the water; and (3) blowing hydrogen gas to flow through the reaction system.

13. The process of claim 12, in which the dehydrating agent is selected from the group consisting of an inorganic salt, an oxide, a hydroxide, a crystalline zeolite and silica gel.

14. The process of claim 12, in which the amount of the dehydrating agent is in the range from 0.1 to 100 molar % based on the starting carbonyl compound.

15. The process of claim 12, in which the water is distilled off by azeotropic dehydration.

16. The process of claim 11, in which the ether compound is produced by the reaction of (a) a hydroxy compound and a carbonyl compound.

17. The process of claim 11, in which the hydroxy compound is represented by the following formula (1):

$$R_1-(OA)_n-OH \qquad (1)$$

wherein, $R_1$ represents a straight or branched alkyl group having 3 to 24 carbon atoms or lower to up to 40 carbon alkenyl or lower to up to 40 carbon alkenyl or a cycloalkyl group having 3 to 12 carbon atoms; A represents an alkylene group having 2 to 12 carbon atoms, which may have a hydroxy group; two or more A's may be the same as or different from one another; and n is a number of 0 to 500.

18. The process of claim 11, in which the carbonyl compound is a ketone or an aldehyde compound represented by the formula (2):

(2)

wherein $R_2$ and $R_3$ represent, independently of each other, a hydrogen atom or a straight or branched alkyl group having 1 to 20 carbon atoms or lower to up to 20 carbon alkenyl; or $R_2$ and $R_3$ may constitute a cyclic structure by bonding each other.

19. The process of claim 11, in which the catalyst is a palladium catalyst supported on carbon, alumina, silica or silica-alumina.

20. The process of claim 11, which is effected under a hydrogen gas pressure of up to 5 kg/cm².

21. A process for producing an ether compound, which comprises reacting a carbonyl compound under a hydrogen gas atmosphere in the presence of a catalyst, while removing water produced by the reaction; and wherein said carbonyl compound is selected from the group consisting of aldehydes and ketones.

22. The process of claim 21, in which the water is removed by at least one method selected from the group consisting of:

(1) being in the presence of a dehydrating agent;

(2) distilling off the water; and (3) blowing hydrogen gas to flow through the reaction system.

23. The process of claim 22, in which the dehydrating agent is selected from the group consisting of an inorganic salt, an oxide, a hydroxide, a crystalline zeolite and silica gel.

24. The process of claim 22, in which the amount of the dehydrating agent used is in the range of from 0.1 to 100 molar % based on the starting carbonyl compound.

25. The process of claim 22, wherein the water is distilled off by azeotropic dehydration.

26. The process of claim 21, in which the ketones or aldehydes have the formula (2):

$$\begin{array}{c} R_2 \\ \phantom{R}\diagdown \\ \phantom{RR}C{=}O \\ \phantom{R}\diagup \\ R_3 \end{array} \qquad (2)$$

wherein $R_2$ and $R_3$ represent, independently of each other, a hydrogen atom or a straight or branched alkyl group having 1 to 20 carbon atoms or lower to up to 20 carbon alkenyl; or $R_2$ and $R_3$ together constitute a cyclic structure.

27. The process of claim 21, wherein the catalyst is a palladium catalyst supported on carbon, alumina, silica or silica-alumina.

28. The process of claim 21, wherein said carbonyl compound is a linear ketone of 1 to 12 carbon atoms, aldehyde of 1 to 12 carbon atoms or a cyclic ketone of 5 to 8 carbon atoms.

29. A process for producing an ether compound, which comprises reacting a hydroxy compound with a carbonyl compound under a hydrogen gas atmosphere in the presence of a catalyst, while removing water produced by the reaction; and wherein said carbonyl compound is selected from the group consisting of aldehydes and ketones; and wherein a molar ratio of said hydroxy compound to said aldehydes or ketones used is from about 50/1 to 1/50, and wherein unreacted reactants therefrom are separated from water, and returned to said process.

30. A process for producing an ether compound, which comprises reacting (a) a hydroxy compound with a carbonyl compound or (b) a carbonyl compound, under a hydrogen gas atmosphere at a pressure of up to 20 kg/cm² in the presence of a catalyst, while removing water produced by the reaction, and wherein unreacted reactants therefrom are separated from water, and returned to said process.

31. A process for producing an ether compound, which comprises reacting a carbonyl compound under a hydrogen gas atmosphere in the presence of a catalyst, while removing water produced by the reaction; and
    wherein said carbonyl compound is selected from the group consisting of aldehydes and ketones, and wherein unreacted reactants therefrom are separated from water, and returned to said process.

32. The process of claim 1, wherein said hydrogen gas is introduced during said reaction.

33. The process of claim 11, wherein said hydrogen gas is introduced during said reaction.

34. The process of claim 21, wherein said hydrogen gas is introduced during said reaction.

35. The process of claim 1, wherein said catalyst comprises a metal or metal compound supported on an inorganic support,
    said metal being selected from the group consisting of palladium, ruthenium, rhodium, platinum, iridium, osmium and rhenium,
    said metal compound being selected from the group consisting of oxides of said metals; and
    said inorganic support being selected from the group consisting of carbon, silica-alumina, zeolite, alumina and silica.

36. The process of claim 11, wherein said catalyst comprises a metal or metal compound supported on an inorganic support,
    said metal being selected from the group consisting of palladium, ruthenium, rhodium, platinum, iridium, osmium and rhenium;
    said metal compound being selected from the group consisting of oxides of said metals; and
    said inorganic support being selected from the group consisting of carbon, silica-alumina, zeolite, alumina and silica.

37. The process of claim 21, wherein said catalyst comprises a metal or metal compound supported on an inorganic support,
    said metal being selected from the group consisting of palladium, ruthenium, rhodium, platinum, iridium, osmium and rhenium;
    said metal compound being selected from the group consisting of oxides of said metals; and
    said inorganic support being selected from the group consisting of carbon, silica-alumina, zeolite, alumina and silica.

* * * * *